US007902362B2

(12) United States Patent
Gao et al.

(10) Patent No.: US 7,902,362 B2
(45) Date of Patent: Mar. 8, 2011

(54) DNA THREADING INTERCALATORS

(75) Inventors: Zhiqiang Gao, Choa Chu Kang Crescent (SG); Fang Xie, Choa Chu Kang Crescent (SG)

(73) Assignee: Agency for Science, Technology & Research, Centros (SG)

( * ) Notice: Subject to any disclaimer, the term of this patent is extended or adjusted under 35 U.S.C. 154(b) by 0 days.

(21) Appl. No.: 12/317,359

(22) Filed: Dec. 22, 2008

(65) Prior Publication Data

US 2009/0233289 A1    Sep. 17, 2009

Related U.S. Application Data

(62) Division of application No. 10/866,370, filed on Jun. 10, 2004, now Pat. No. 7,479,557.

(51) Int. Cl.
*C07F 15/00* (2006.01)
*C12Q 1/68* (2006.01)

(52) U.S. Cl. .................................. 546/2; 435/6; 546/10

(58) Field of Classification Search ................ 546/2, 10, 546/66; 435/6
See application file for complete search history.

(56) References Cited

U.S. PATENT DOCUMENTS

| 6,368,807 B2 | 4/2002 | Makino et al. | |
|---|---|---|---|
| 2001/0014452 A1 | 8/2001 | Makino et al. | |
| 2002/0012917 A1 | 1/2002 | Makino et al. | |
| 2005/0214471 A1* | 9/2005 | Theobald et al. ............. | 427/402 |

FOREIGN PATENT DOCUMENTS

| BE | 644413 | * | 6/1964 | ................ 546/66 |
|---|---|---|---|---|
| GB | 1064627 | | 4/1967 | |
| JP | 2001165894 | | 6/2001 | |
| WO | 0240479 A1 | | 5/2002 | |
| WO | 02057488 A2 | | 7/2002 | |
| WO | 02066679 A1 | | 8/2002 | |
| WO | 02053571 A1 | | 11/2002 | |

OTHER PUBLICATIONS

Bilyk, A. et al.: Guest-induced assembly of a chiral metallomacrocycle. J. Chem. Soc. Chem. Commun. vol. 16, pp. 1697-1698, 1995.*
Stellet, V. et al.: Self-stacking of naphthalene bis(dicarboximide)s probed by NMR. J. Chem. Soc. Perkin Trans. 2, pp. 1547-1558, 1999.*
Ghiggino, K. P. et al.: Modulating electron transfer in a simple bichromophoric system employing axial-ligation as an organising precept. J. of the inclusion phenom. and Macrocyc. Chem. , vol. 49, pp. 27-32, 2004.*
Compound with RN 182321-03-5.*
Takenaka et al., "DNA sensing on a DNA probe-modified electrode using ferrocenylnaphthalene diimide as the electrochemically active ligand", Anal Chem 72:1334-41 (2000).
Dixon et al., "Effect of DNA scaffolding on intramolecular electron transfer quenching of a photoexcited ruthenium (II) polypyridine naphthalene diimide", Inorg. Chem. 38:5526-34 (1999).
Zhang et al. "Enzyme-amplified amperometric detection of 3000 copies of DNA in a 10-µL droplet at 0.5 fM concentration", Anal Chem 75:3267-3269 (2003).
Dequaire et al., "Screen printing of nucleic acid detecting carbon electrodes", Anal Chem 74:4370-4377 (2002).
Patolsky et al., "Amplified DNA detection by electrogenerated biochemiluminescence and by the catalyzed precipitation of an insoluble product on electrodes in the presence of doxorubicin intercalator", Angew. Chem. Int. Ed. 41(18):3398-3402 (2002).
Armistead et al., "Modification of indium tin oxide electrodes with nucleic acids: detection of attomole quantities of immobilized DNA by electrocatalysis", Anal Chem 72:3764-70 (2000).
Gore et al., "Detection of attomole quantitites of DNA targets on gold microelectrodes by electrocatalytic nucleobase oxidation", Anal Chem 75:6586-6592 (2003).
Xie e al., "Amperometric detecation of nucleic acid at femtomolar levels with a nucleic acid/electrochemical activator bilayer on gold electrode", Anal Chem 76:1611-1617 (2004).
Steullet et al., "Studies of Naphthalene diimides as DNA-binding agents", First International Electronic Conference on Synthetic Organic Chemistry, pp. 1-17, Sep. 1-30, 1997.
Doherty et al., Electrocatalytic Oxidation of Ascorbic Acid at [Osmium(2.2'-bipyridyl)-(poly-4-vinylpyridine)10CI]CI Modified Electrodes; Implications for the Development of Biosensors Based on Osmium-containing Redox Relays, Analysis, vol. 120:2371-2376 (Sep. 1995).
Hossian et al., "Syntheses, Spectroelectrochemistry and Photoinduced Electron-Transfer Processes of Novel Ru and Os Dyad and Triad Complexes with Functionalized Diimide Ligands", Collections of Czechoslavak Chemical Communications, vol. 66(2), p. 307-337 (2001).
Sato et al. "Ferrocenyl naphthalene diimide can bind to DNA RNA hetero duplex: potential use in an electronchemical detection of MRNA expression", Journal of Organometallic Chemistry, 637-639, 476-483 (2001).
Schuetz et al. "Basically alkyated imides of naphthalene-1, 4, 5, 8, -tetracarboxylic acid and their chemotherapeutic properties", Arzneimittel-Forschung vol. 21(6) p. 739-763 (1971).

(Continued)

*Primary Examiner* — Charanjit S Aulakh
(74) *Attorney, Agent, or Firm* — Stout, Uxa, Buyan & Mullins; Carlos A. Fisher

(57) ABSTRACT

The invention is directed to a compound having the general formula (1):

$(V_aM_a)Z_a$—$L_a$—N[naphthalene diimide core]N—$L_b$—$Z_b(M_bV_b)$ wherein each of $L_a$ and $L_b$ is an independently selected from a linking moiety comprising 0 to 10 main chain atoms, optionally substituted;
each of $Z_a$ and $Z_b$ is an independently selected complexing moiety comprising at least one nitrogen atom;
either both or one of $Z_a$ and/or $Z_b$ is coordinatively bonded to a respective transition metal complex $M_a V_a$ and $M_b V_b$ through said nitrogen atom, wherein
each of $M_a$ and $M_b$ is an independently selected transition metal, and each of $V_a$ and $V_b$ is an independently selected valence group.

17 Claims, 10 Drawing Sheets

OTHER PUBLICATIONS

Steullet V et al. "Design synthesis and DNA-cleavage of Gly-Gly-His-napthalene diimide conjugates" Bioorganic and Medicinal Chemistry letters, vol. 9 (20) p. 2935-2940 (1999).

Takenaka S., "Synthetic threading intercalators as a new analytical probe for necleic acid and gene detection", Bunseki Kagaku, vol. 48(12), p. 1095-1105 (1999).

Takenaka S. et al. "Selective stabilization of a bulged duplex of d(GCGAAAGCG) oligonucleotide by thymine base-substituted naphthalene diimide", Chemical Communications (Cambridge) vol. 1 p. 115-116 (1997).

Zhao W. et al. "Preparation and electrochemistry of aromatic polymides on the electrode surface" Quingado Daxue Xubao, Gongcheng Jishuban BianJibu, vol. 11(4). p. 1-10 (1996).

Supplemental European Search Report in related European Application No. 05742652.0 dated Apr. 22, 2010.

Tansil et al., "An ultrasensitive nucleic acid biosensor based on the catalytic oxidation of guanine by a novel redox threading intercalator", *Chem. Commun.*, 2005, pp. 1064-1066.

Tansil et al., "Direct Detection of DNA with an Electrocatalytic Threading Intercalator", *Anal. Chem.*, Jan. 1, 2005, vol. 77, No. 1, pp. 126-134.

* cited by examiner

DNA THREADING INTERCALATORS

RELATED APPLICATION

This application is a divisional of U.S. patent application Ser. No. 10/866,370, filed Jun. 10, 2004, the disclosure of which is incorporated in its entirety herein by reference.

This invention relates to novel organometallic compounds, in particular, novel naphthalene diimide derivatives. The invention also relates to processes for preparing these compounds, the uses of these compounds, and methods of detecting nucleic acids using these compounds.

BACKGROUND OF THE INVENTION

Over the past few decades, nucleic acid technology has grown to assume an indispensable role in many areas of genetic research. Many useful applications such as genotyping, diagnosis of diseases, analysis of biological samples, and many other diagnostic applications have been spawned from research efforts put into this field. Efforts are currently being focussed on the development of DNA biosensors that employ efficient nucleic acid amplification and detection techniques to achieve better sensitivity and specificity within a short turnaround time.

A fundamental process carried out in a DNA biosensor is the transduction of a nucleic acid recognition event, such as the hybridisation of a probe nucleotide sequence with a single stranded DNA from a sample, into a signal that is detectable by conventional detection methods. Amongst the various types of detection methods known in the art, such as optical (light), electrical (current), electrochemical and frequency detection methods, optical detection methods have become very widely employed.

Optical detection methods typically require the use of fluorescent molecules. Hybridisation of target nucleotide sequences labelled with fluorescent molecules (e.g. ethidium bromide) can be detected by monitoring the increase in fluorescence that accompanies the hybridisation between the probe and the target nucleotide sequence. When employed in conjunction with surface modification techniques, fluorescent labels have enabled high density DNA arrays to be constructed. Massively parallel reactions carried out on high density arrays are able to rapidly elucidate nucleic acid sequences, and thus substantially reduce the amount of time required for analysis.

However, fluorescent labels suffer from several shortcomings. For example, tedious procedures are involved in the attachment of the fluorescent molecule to the target DNA. Moreover, only a few of the fluorescence-based detection techniques have sufficiently high sensitivities for the detection of DNA at sub-nanomolar levels. In order to avoid such problems, electrochemical detection methods have been proposed for carrying out ultrasensitive detection of DNA hybridisation events.

Electrochemical DNA biosensors have been reported since about 1990. A wide variety of methods, such as the use of gold nanoparticles, the direct oxidation of guanine, as well as the use of DNA intercalators, have been developed for facilitating electrochemical detection methods. It was known that unlike fluorescent indicators, the use of DNA intercalators as hybridization indicator does not involve the tedious labelling of the target DNA with the fluorescent indicator, as is commonly employed in conventional DNA detection techniques. Additionally, expensive optical equipment are not needed. The inherent miniaturization of electrochemical biosensors and their compatibility with advanced semiconductor technologies also promise to provide a simple, accurate and inexpensive platform for nucleic acid assays.

Both low- and high-density electrochemical DNA sensor arrays have been successfully fabricated. At present, high-density fluorescent microarrays are substantially cheaper to manufacture and implement than high density electrochemical sensor arrays. However, low-density electrochemical sensor arrays have the following advantages over fluorescent arrays: (i) they provide a cost-effective alternative to expensive optical devices; (ii) when coupled with catalysis, they are ultrasensitive; (iii) they provide rapid, direct, turbid and light absorbing-tolerant detection of hybridisation events; and (iv) they are portable, robust, cheap and require only easy-to-handle electrical components. These advantages render electrochemical biosensors suitable for field tests and home-care use.

Two fundamental issues that need to be addressed in the development of catalytic/enzymatic biosensors are the large background noise accompanying the signal and the sensitivity of the sample assay. Currently, many electrochemical biosensors are still plagued with low signal/noise ratios. Most DNA intercalators not only bind to double-stranded DNA (ds-DNA) but also, to a lesser extent, to single-stranded DNA (ss-DNA) molecules by electrostatic interaction. Several approaches for obtaining improved intercalators have been investigated.

Takenaka et al. synthesized a ferrocene-grafted naphthalene diimide (ND) threading intercalator that was reported to bind to ds-DNA more selectively than usual intercalators (Anal. Chem. 2000, 72 1334-1341). Similarly, Makino et al. disclosed a ferrocene-grafted naphthalene diimide threading intercalator reportedly required an electric potential of less than 450 mV for electrochemical detection (U.S. Pat. No. 6,368,807; US Patent Application No. 20020012917 A1). Steullet et al. disclosed a ND threading intercalator in which a pair of ruthenium complexes are each located at the termini of the side chains of the ND scaffold. Each ruthenium complex is coordinatively bonded to a bipyridine group that is carried on a straight-chained amide side chain (First International Electronic Conference on Synthetic Organic Chemistry—ECSOC-1, E0003, Sep. 1-30, 1997). The effect of DNA scaffolding on intermolecular electron transfer quenching of a photoexcited ruthenium (II) polypyridine naphthalene diimide was investigated in a further study, and it was found that the pendant chromophore interacted weakly with the DNA duplex (Inorg. Chem. 1999, 38, 5526-5534).

Further attempts were made by other groups to enhance the sensitivity and to lower the detection limit of detection methods relying on ND threading intercalators by incorporating chemical and biological amplification mechanisms. (Anal. Chem. 2003, 75, 3267-3269; Anal. Chem. 2002, 74, 4370-4377; Patolsky, F., Katz, E., Willer, I. Angew. Chem., Int. Ed. 2002, 41, 3398-3402). Thorp et al. proposed an electrocatalytic scheme for the direct detection of DNA, using the homogeneous electrocatalysts ruthenium-2,2'-bipyridine or osmium-2,2'-bipyridine complex (Anal. Chem. 2000, 72, 3764-3770; Anal. Chem. 2003, 75, 6586-6592). Others have used DNA-enzyme conjugates as bio-electrocatalysts for the electrochemical transduction of DNA recognition events. Bio-catalytic conjugates that are able to associate with DNA recognition events and stimulate the precipitation of an insoluble product on electrodes were also used as an amplification system for DNA sensing (Anal. Chem. 2004, 76, 1611-1617).

In studies where transitional redox active metal complexes were used as homogenous catalysts, the analytical signal obtained was found to be superimposed onto an intrinsically large and fluctuating background current which obscured the analytical signal indicating the occurrence of hybridisation. The large background current was determined to be the result of the direct oxidation of the catalyst, and the catalytic oxidation of the oligonucleotide capture probes (CP) by the catalyst (Anal. Chem. 2000, 72, 3764-3770; Anal. Chem. 2003, 75, 6586-6592). One solution that has been developed towards eliminating the catalytic oxidation current is to replace the oligonucleotide CP with peptide nucleic acid. However, the problem of direct oxidation of the catalyst was not adequately dealt with. In enzyme-based DNA assays, the background current is known to be directly associated with non-DNA related enzyme uptake, such as non-specific adsorption and electrostatic interaction.

Efforts to bring about the reduction of the background current in catalytic DNA biosensors are currently being made. In one recent study, it was found that background current can be reduced by constructing the DNA biosensor in a bilayer configuration (Analyst, 1995, 120, 2371-2376). As few as 600 copies of target DNA molecules in 1.0 μL droplets were successfully detected with a biosensor having such a bilayer configuration.

Despite the developments that have taken place, there still exists limitations in the present catalytic biosensors for which continuing efforts are needed to improve their performance without incurring prohibitively high manufacturing costs.

Accordingly, it is an object of the present invention to provide compounds which can be used as DNA threading intercalators that have improved detection sensitivity, which are inexpensive to manufacture and simple to use, and thus would enable microarraying techniques to be more widely utilised in biomedical research and healthcare.

SUMMARY OF THE INVENTION

The present invention provides naphthalene diimide derivatives tagged with electrocatalytic transition metal pendant groups which can be used as DNA intercalating compounds. In one aspect, the invention is directed to a compound having the general formula (I):

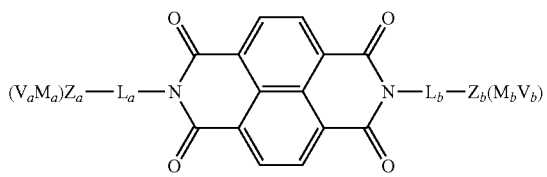

wherein
each of $L_a$ and $L_b$ is an independently selected linking moiety comprising 0 to 10 main chain atoms, optionally substituted;
each of $Z_a$ and $Z_b$ is an independently selected complexing moiety comprising at least one nitrogen atom;
either both or one of $Z_a$ and/or $Z_b$ is coordinatively bonded to a respective transition metal complex $M_a V_a$ and/or $M_b V_b$ through said nitrogen atom, wherein
each of $M_a$ and $M_b$ is an independently selected transition metal, and
each of $V_a$ and $V_b$ is an independently selected valence group,
with the proviso that the following compounds are excluded:

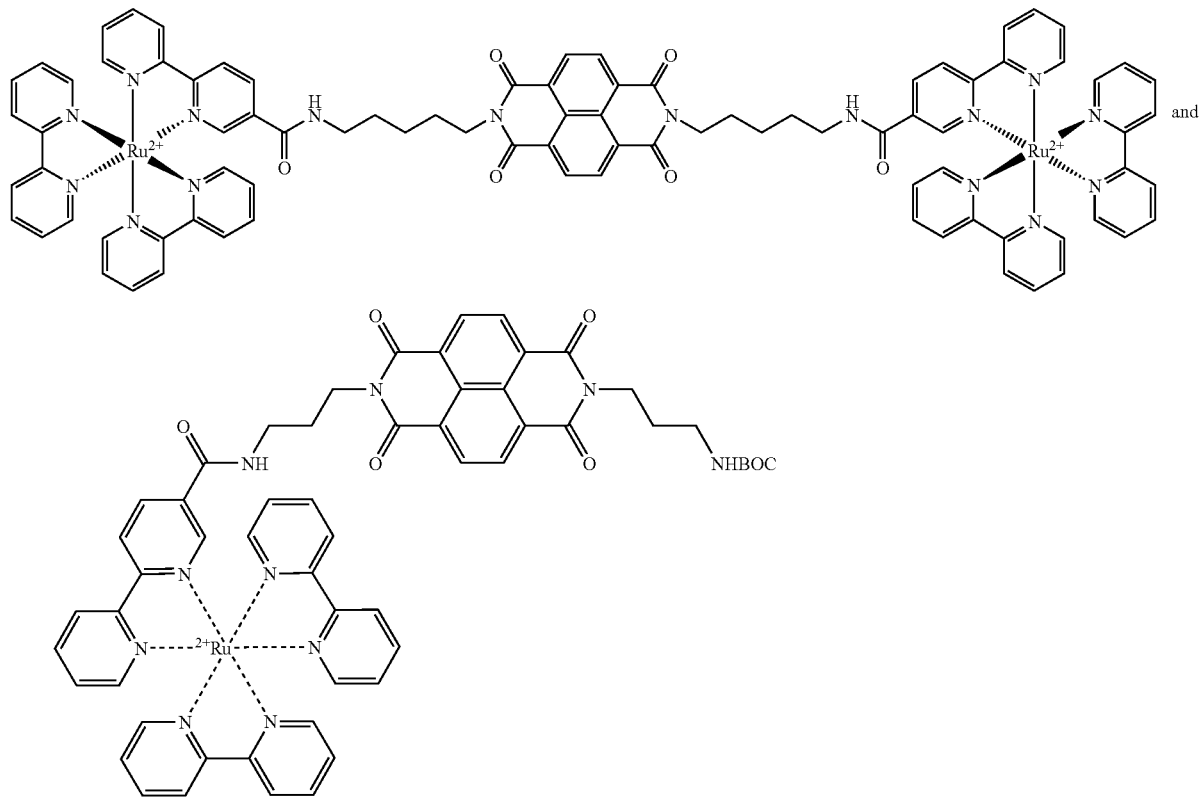

which are respectively disclosed in [E0003] First International Electronic Conference on Synthetic Organic Chemistry (ECSOC-1), www.mdpi.org/ecsoc/, Sep. 1-30, 1997, and Inorganic Chem 1999, 38, 5526-5534.

The invention is further directed to a compound having the general formula (1i):

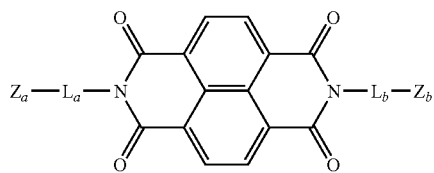

wherein
each of $L_a$ and $L_b$ is an independently selected linking moiety comprising 0 to 10 main chain atoms, optionally substituted, and each of $Z_a$ and $Z_b$ is an independently selected complexing moiety comprising at least one nitrogen atom;

with the proviso that the following compounds are excluded:

a)

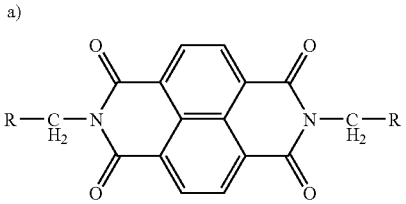

wherein both R are identical and are selected from the group consisting of:

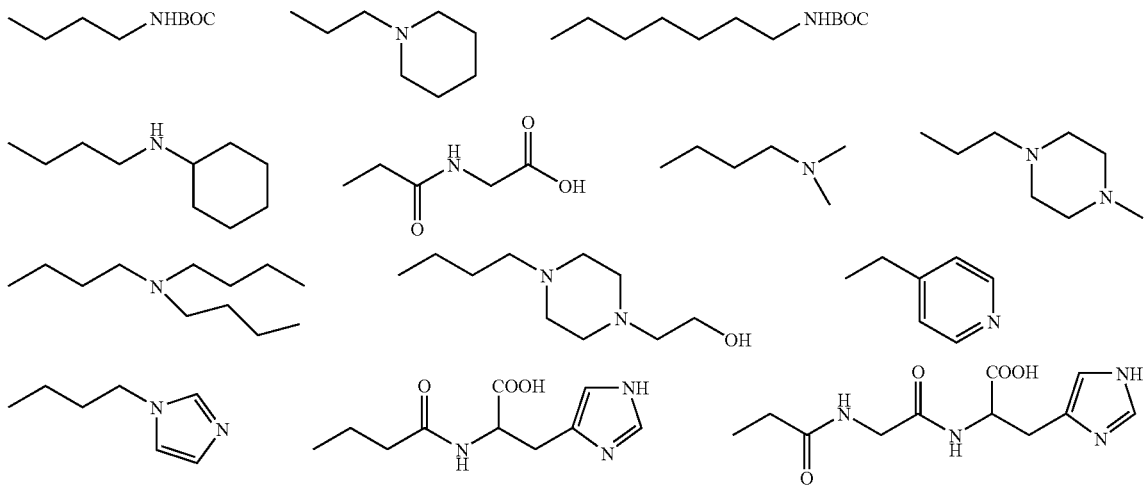

b)

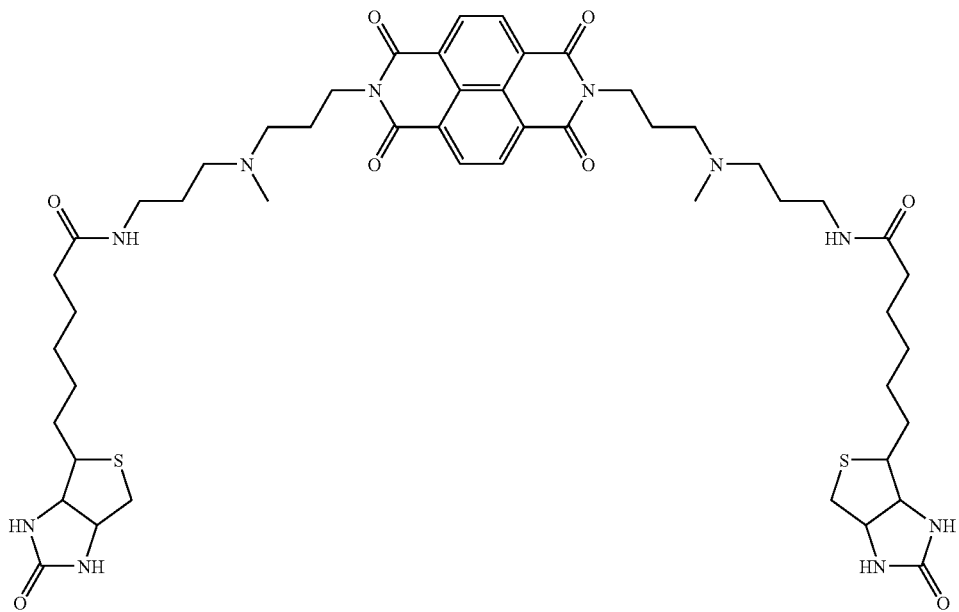

c) 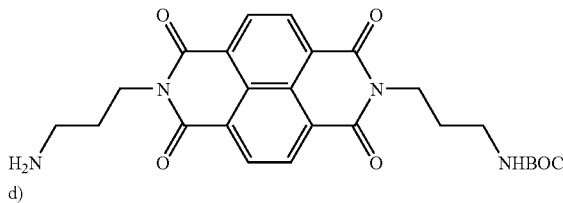

d) 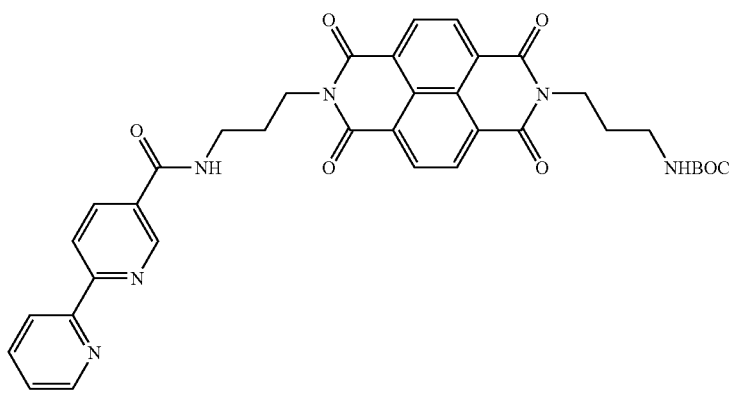

This means that the specific symmetrical compounds defined in a) and b) that are disclosed in [E0003] First International Electronic Conference on Synthetic Organic Chemistry (EC-SOC-1), www.mdpi.org/ecsoc/, Sep. 1-30, 1997 or Inorganic Chem 1999, 38, 5526-5534 are no compounds of the present invention. The same applies to the specific asymmetrical compounds defined in c) and d) which are also disclosed in these two references. However, any other sub-combination using a radical R as depicted in a) which results in an asymmetrical compound is part of the invention.

In another aspect, the invention is directed to a process for producing a compound having the general formula (I), comprising:

reacting 1,4,5,8-naphthalene tetracarboxylic dianhydride with a primary amine having the formula (IV):

and/or a primary amine having the formula (V):

thereby forming a naphthalene diimide intermediate; and reacting the naphthalene diimide intermediate with a transition metal complex, thereby coordinatively bonding the metal complex to the at least one nitrogen atom in each of $Z_1$ and/or $Z_2$.

The invention is also directed to the use of the compound of formula (I) as a double stranded DNA threading intercalator.

In a further aspect, the invention is directed to a method of detecting a nucleic acid, comprising:

contacting at least one capture probe immobilised on a substrate with the nucleic acid, said capture probe having a nucleotide sequence complementary to the sample, thereby hybridising the nucleic acid with the capture probe to form a hybrid;

contacting the hybrid with a DNA threading intercalator having the general formula (I), thereby intercalating the hybrid;

contacting an organic acid with the intercalated hybrid;

applying an oxidising or reducing potential to the organic acid; and determining the electrochemical response of the organic acid.

These aspects of the invention will be more fully understood in view of the following description, drawings and non-limiting examples.

DETAILED DESCRIPTION

Figure 1:
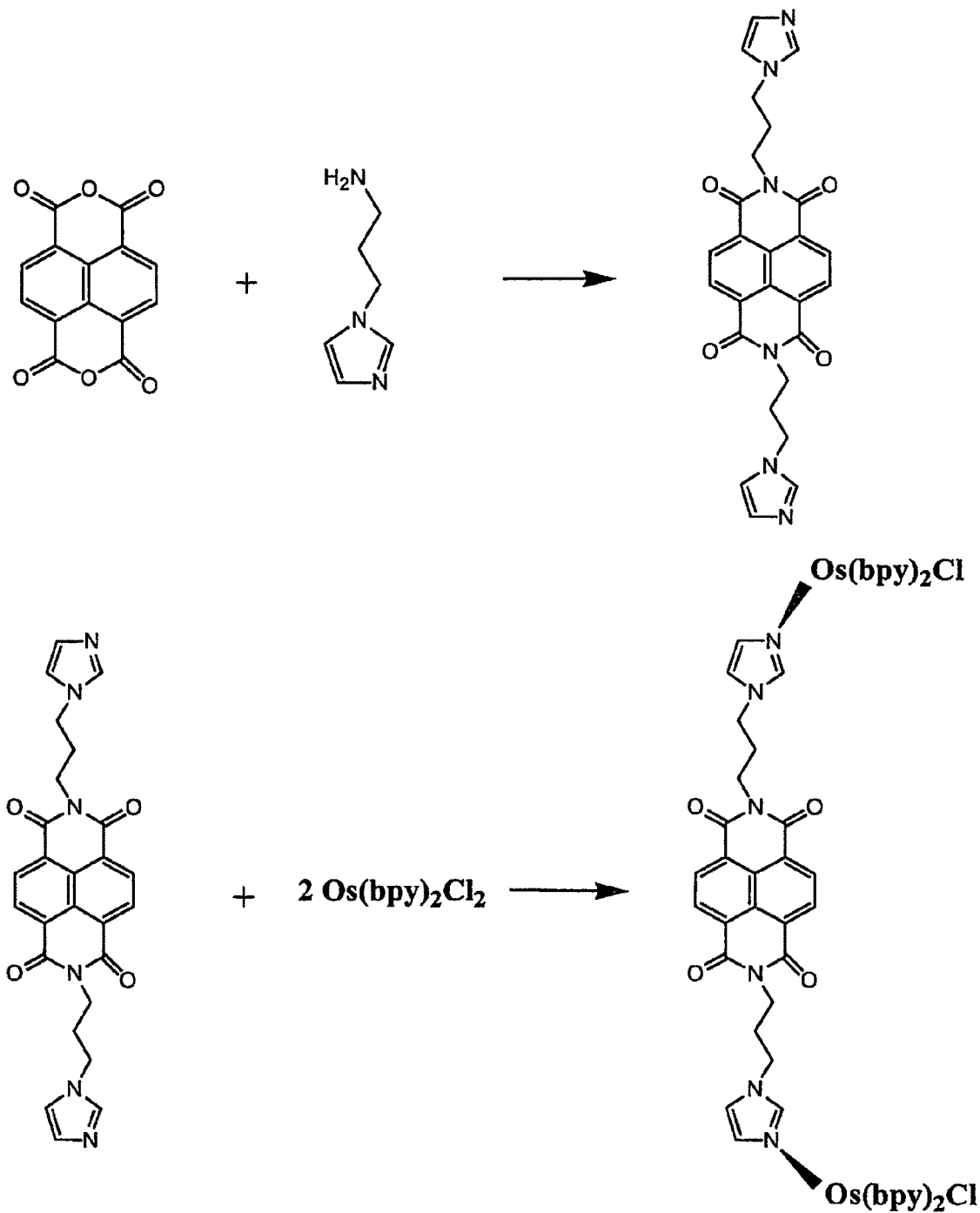
FIG. 1 depicts a general synthesis scheme for obtaining the compounds of formula (I).

The present invention is based on the finding that naphthalene diimide compounds carrying redox-active transition metal complexes that are attached to the central diimide scaffold via complexing functionalities display excellent characteristics as double stranded DNA threading intercalators. As compared to the parent compound 1,4,5,8-naphthalene diimide, the compound of the invention binds more strongly to double stranded DNA. Without wishing to be bound by theory, the naphthalene diimide groups bind to dsDNA in a "classical" threading intercalation model, while the pendant transition metal complex group interacts electrostatically with DNA, thereby reinforcing the intercalation. Additionally, the redox active transition metal groups provide electrocatalytic activity which can be used to improve the electrochemical response of the intercalated complex. Consequently, biosensors employing the compounds of the invention as intercalators can achieve very high levels of detection sensitivity. It was found in the present invention that under optimised conditions, a specific DNA sequence at concentrations of about 0.2 to 600 pM can be reliably detected with biosensors using the present compounds as intercalators. Under certain conditions, the detection limit has been found to be as low as about 100 fM.

Some advantages of the present invention are as follows. Firstly, the compounds of formula (I) are water soluble yet very stable under ambient conditions, displaying high electron mobility, good kinetics and electrocatalytic efficiency. Coupled with the electroactive and electrocatalytic ability of the transition metal complex present in the compound, these characteristics provide an interesting means to detect a target DNA sequence at high sensitivity. Furthermore, it has been found that the intercalation strength of the present compound towards nucleic acids and proteins is very strong, thus rendering them as suitable candidates of cancer and tumour drugs. These compounds can be used in a variety of applications, such as electrochemically active tags for biological molecules, or can be functionalised to react with bioaffinitive species such as biotin, digoxin, proteins, antigens, and antibodies, thereby providing the present compounds with sufficient bioaffinity for use in bioassays.

Each of $L_a$ and $L_b$ in the above general formula (I) denotes a linking moiety that is located between the complexing moiety and the naphthalene diimide scaffold. $L_a$ and $L_b$ are chosen independently, each comprising 0 to 10 main chain atoms. In certain embodiments of the invention, the linking moieties $L_a$ and $L_b$ each comprises 2, 3, 4, or 5 main chain atoms. For illustrative purposes, if a 1,4-substituted cyclohexyl or phenyl group, for example, is comprised in the linking moiety, this cyclohexyl or phenyl (aryl) group then contributes 4 main chain carbon atoms to the linking moiety. The hydrogen atoms bonded to each main chain atom are optionally substituted, for example, with halogen, amino, hydroxy or carboxyl groups. The main chain of the linking moiety may consist solely of carbon atoms, or it may comprise carbon atoms interrupted by nitrogen, oxygen or sulfur atoms (i.e. a heterochain). This means that the linking moiety can comprise an ether group, a thioether group, an ester group, or an amide group, for example (see GB Patent 1,064,627 or Inorganic Chem 1999, 38, 5526-5534, for example). If there are zero main chain atoms (i.e. the linking moiety is absent), the nitrogen atom on the naphthalene diimide scaffold is directly bonded to the complexing moiety. By varying the chain length of the linking moiety, it is possible to vary the interaction between the present inventive compound and the hybridised probe.

$L_a$ and $L_b$ as defined in formula (I) above can be any straight chained or branched, substituted or unsubstituted alkyl, alkenyl, alkynyl, aryl, acyl, cycloalkyl, cycloalkylalkyl, cycloalkenyl, or arylkyl group/radical. When the compounds of the present invention are used as DNA intercalators, $L_a$ and $L_b$ are preferably saturated, branched or straight-chained, alkyl groups. The number of carbon atoms in the linking moiety may be increased or decreased to vary the length of the carbon chains carrying the transition metal groups, and thus provide a means to vary the distance between the transition metal groups.

Alkyl groups may be straight chained or branched. This also applies if the alkyl groups are present in other linking moieties such as acyl groups, carbonyl groups or in amino groups, where they are substituents of these groups. In one embodiment, each of $L_a$ and $L_b$ is an aliphatic saturated hydrocarbon chain. Examples of preferred alkyl groups that are used in compounds having formula (I) are methyl, ethyl, propyl, isopropyl, n-propyl, butyl, n-butyl, tert-butyl, pentyl, n-pentyl, iso-pentyl, n-hexyl, iso-hexyl, heptyl, octyl, nonyl and decyl groups.

Examples of alkenyl groups include all aliphatic hydrocarbons having at least one carbon-carbon double bond. In this context, alkenyl radicals when used as main chain radicals can have up to 10 main chain carbon atoms.

Examples of alkynyl radicals include straight-chained or branched hydrocarbon atoms which contain at least one triple carbon-carbon double bond. In this context, alkynyl radicals when used as main chain radicals may have up to 10 main chain carbon atoms.

Examples of aryl radicals, include all carbocyclic or heterocyclic aromatic radical, preferably phenyl, naphthyl, tolyl or heteroaryl. Aryl radicals may also be unsubstituted or substituted with substituents such as halogens, alkyls, hydroxyls, and carboxyls, for example.

Cycloalkyl radicals are saturated cyclic hydrocarbons which normally contain three to eight ring carbon atoms, preferably five or six ring carbon atoms. Cycloalkyl radicals may also be substituted, for example, by one or more identical or different alkyl radicals, such as methyl or ethyl groups. Examples of cycloalkyl radicals are cyclopropyl, cyclobutyl, cyclopentyl, cyclohexyl, cycloheptyl and cyclo-octyl. Examples of substituted cycloalkyl radicals are 4-methyl-cyclohexyl or 2,3-dimethylcyclopentyl, for example.

Cycloalkylalkyl radicals are saturated hydrocarbons which are derived from a cycloalkyl-substituted alkyl group. The cycloalkyl group normally has five to six ring carbon atoms. Examples of cycloalkylalkyl radicals are cyclopentylmethyl, cyclopentylethyl, cyclohexylethyl and cyclohexylmethyl. Cycloalkylalkyl radicals may in turn be substituted.

Cycloalkenyl radicals are unsaturated cyclic hydrocarbons which normally contain three to eight ring carbon atoms. Cycloalkenyl radicals have at least one carbon-carbon double bond, but may have 2 or more double bonds. Cycloalkenyl radicals may in turn be substituted.

Arylkyl radicals which may be used in particular are benzyl, phenethyl and naphthylmethyl groups. All groups may be optionally substituted or polysubstituted, for example, with a halogen, hydroxy, amino, nitro, nitrile, alkoxy, or a carboxyl group.

Halogen as used herein refers to any one of chlorine, bromine, fluorine and iodine.

In the context of the invention, the last main chain atom of the linking moiety is the atom that is bonded to either a carbon atom or a nitrogen atom of the complexing moiety. The complexing moiety may be, for example, a heterocyclic aromatic or heterocyclic aliphatic ring system, or a hetero-aliphatic chain such as an amino group). In accordance with this definition, compounds in which the -L-Z— moiety has, for example, the following structure (as disclosed in [E0003] First International Electronic Conference on Synthetic Organic Chemistry (ECSOC-1), www.mdpi.org/ecsoc/, Sep. 1-30, 1997):

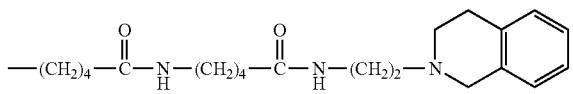

would be considered to have 14 main chain atoms in the linking moiety, i.e. more than 10 main chain atoms, and are thus not part of the invention.

In formula (I), each of the complexing moieties $Z_a$ and $Z_b$ comprises at least one nitrogen atom. Each of $Z_a$ and $Z_b$ is independently selected, meaning that $Z_a$ and $Z_b$ can be identical or different. The at least one nitrogen atom provides a lone pair of electrons that enables coordinative bonding to a suitable transition metal complex.

The complexing moieties $Z_a$ and $Z_b$ can be any suitable radical having a nitrogen atom. Examples of such radicals include aliphatic and aromatic moieties carrying amino or amide groups, as well as aromatic and aliphatic radicals carrying —N═O, —C≡N, —N═N—, or —C═N— groups, for example. A suitable class of aliphatic radicals are primary and secondary amino groups. In a specific embodiment in which a primary or secondary amino group is used, the nitrogen atom of the amino group is bonded to an aliphatic alkyl group having 1 to 6 main chain carbon atoms. Examples of such alkyl groups include methyl, ethyl, propyl, propyl, butyl, pentyl, hexyl and isomers thereof.

In some embodiments of the invention, the complexing moieties $Z_a$ and $Z_b$ may, in addition to nitrogen-containing functional groups or moieties, include other suitable functional groups which are able to displace weaker ligands on the transition metal complex. Examples of such functional groups include —COOH, —COH, —COOR, —SO₃H, for example.

In another embodiment, the complexing moiety comprises a heterocycle. Suitable heterocycles include both non-aromatic and aromatic heterocycles (unsaturated and saturated). The heterocycle can either be monocyclic or bicyclic, in which ring atoms are selected from the group consisting of C, N, O, and S. Suitable heterocycles include imidazole, triazine, pyrazine, acridine, azepine, aziridine, benzodiazine, diazine, isoquinoline, lactam, morpholine, oxazine, phenanthridine, phenanthroline, piperazine, pteridine, purine, pyridine, pyrrole, pyrrolidine, quinoline, quinolizine, thiadiazine, thiazine, triazine and tropane, for example. Heterocycles that are presently preferred in the invention are imidazole, purine, phenanthroline, piperazine, and pyridine. In a specific embodiment in which the complexing moiety is imidazole, one of the two ring nitrogen atoms is bonded to the linking moiety, while the other ring nitrogen atom is complexed with a transition metal complex.

Either both or one of $Z_a$ and/or $Z_b$ is coordinatively bonded to a respective transition metal complex $M_a V_a$ and $M_b V_b$, where each of $M_a$ and $M_b$ is an independently selected transition metal, and each of $V_a$ and $V_b$ is an independently selected valence group. The selection of a suitable transition metal can be based on the desired electrochemical response that is necessary for hybridisation detection.

Any transition metal that exhibits an adequate level of redox activity suitable for producing a detectable electrochemical response may be used. Any metal selected from Group 3 to 12, preferably Groups 5 to 11, and more preferably Groups 7 to 10 (IUPAC, 1990), may be used. The transition metal $M_a$ and $M_b$ may be present as a charged or uncharged species, depending on its oxidation state. Typically, each transition metal species will be present as a charged cation, i.e. it will have a positive charge of +1, +2, +3 or +4. Specific examples of transition metals that are suitable in the invention include, but are not limited to, ruthenium, osmium, rhenium, iron and platinum. Due to the high catalytic efficiency as well as low redox potentials associated with osmium complexes, osmium is presently preferred.

In order to satisfy the coordination valence of $M_a$ and/or $M_b$, the valence group $V_a$ and $V_b$ can comprise any number or type of valence members. For example, if $M_a$ has a coordination valence of 6, $M_a$ can be coordinatively bonded to 5 or less valence members in which each valence member contributes 1 pair of unbonded electrons for establishing a coordinative bond with $M_a$. The complexing moiety takes up at least one coordination valence from $M_a$ in order for it to be coordinatively bonded to the transition metal. If the complexing moiety is a bivalent species such as bipyridine, then it will take up 2 coordination valences from the transition metal. Examples of valence members which can be used include halide, pyridine, bipyridine, phenanthroline, imidazole, dipyridophenazine, porphyrin and their derivatives.

One class of compounds falling within the definition of formula (I) and which are suitable as DNA threading intercalators are asymmetrical compounds in which the complexing moieties $Z_a$ and $Z_b$ are different. Asymmetrical compounds of formula (I) may carry one or two transition metal complexes. Both $Z_a$ and $Z_b$ may each be bonded to the same type of transition metal complex or two different types of transition metal complexes (e.g. Za is grafted with an osmium complex and Zb is grafted with a rubidium complex). Where only one transition metal complex is present, either $Z_a$ or $Z_b$ will be bonded to the transition metal complex. In order to obtain a compound having such a structure, $Z_a$ and $Z_b$ can be chosen accordingly. For example, $Z_a$ may be chosen from a suitable moiety that has a nitrogen atom with a free electron pair which can be complexed with a transition metal complex, while $Z_b$ may be chosen from any moiety which may not have any available free electron pair for complexation. In this example, $Z_b$ can be any suitable moiety, as long as it does not adversely affect the intercalating properties of the compound or hinder the synthesis of the compound.

In one embodiment, the asymmetrical compound of the invention comprises imidazole and morpholine complexing moieties. The imidazole complexing moiety establishes a coordinative bond with the transition metal complex while the morpholine complexing moiety is not bonded to any transition metal complex. This asymmetrical intercalator carries only one transition metal pendant group. Other combinations of $Z_a$ and $Z_b$ that are contemplated in the invention include imidazole/bypyridine, phenanthroline/imidazole, and pyridine/bipyridine.

In a particularly preferred embodiment, the compound of formula (I) is an asymmetrical compound having the formula (II):

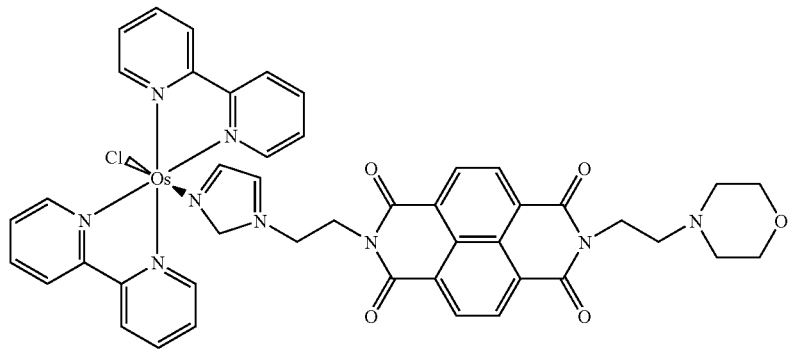

In the above formula (II), the linking moieties are ethyl radicals. One complexing moiety is an imidazole while the other complexing moiety is a morpholine. In this particular embodiment, only one transition metal complex is present, and is coordinatively bonded to the imidazole group. The morpholine group is not bonded to any transition metal complex. The transition metal present in this embodiment is osmium, and the valence group comprises bipyridine and chloride ligands. The overall charge due to each osmium cation may be +1 or +2.

In another particularly preferred embodiment, the compound of formula (I) is a symmetrical compound having the formula (III):

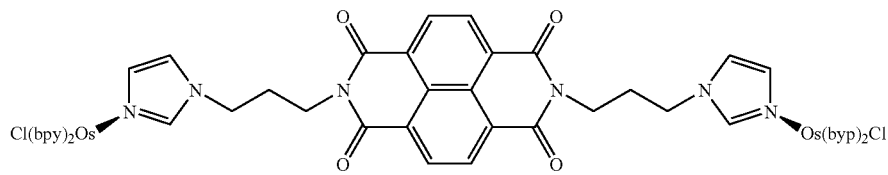

It can be seen from the above formula (III) that the two linking moieties are propyl radicals. The two complexing moieties are imidazole groups; and the two transition metal complexes present are osmium complexes. Each osmium complex comprises an osmium cation, 2 bipyridine ligands and 1 chlorine ligand, thereby producing the overall charge of +2 in the compound of formula (III) in its unoxidised state, or +4 in its oxidised state, the oxidation state of osmium in this case being either Os(III) or Os(IV), respectively.

All possible isomers of the compounds having the above specific formulas, well as mixtures of the above two or more of such compounds in all possible ratios are within the scope of the invention.

The invention is further directed to the intermediate compounds which are used to produce the compound as defined in claim 1. These intermediate compounds are primary derivatives of naphthalene diimides obtained by reacting 1,4,5,8,-naphthalene tetracarboxylic dianhydride with primary amines which have structures that correspond to the linking moiety and complexing moieties in the desired compound of formula (I). In other words, an amine having the formula (IV):

$$H_2N\text{-}L_a\text{-}Z_a$$

and/or an amine having the formula (V):

$$H_2N\text{-}L_b\text{-}Z_b$$

wherein $L_a$, $L_b$, $Z_a$ and $Z_b$ have the same meaning as defined in the above formula (I). If the amines of formula (IV) and (V) are identical, in other words, a single amine is used, then the corresponding intermediate will be symmetrical. However, if two different amines are used, asymmetrical intermediates will be obtained.

Symmetrical intermediate compounds which are disclosed in the reference [E0003] First International Electronic Conference on Synthetic Organic Chemistry (ECSOC-1), www-.mdpi.org/ecsoc/, Sep. 1-30, 1997 and excluded from the invention. However, sub-combinations of linkers and complexing moieties disclosed therein which lead to asymmetrical compounds are part of the present invention.

The invention is also directed to a method of preparing compounds having formula (I). The general synthesis route for forming the compound of formula (I), which is illustrated in FIG. 1, is a 2-step process. The synthesis route is described in detail as follows. First, a naphthalene diimide derivative (intermediate) is formed by reacting 1,4,5,8-naphthalene tetracarboxylic dianhydride (herein after referred to as 'dianhydride') with one or two primary amines which have structures that correspond to the linking moiety and complexing moieties in the desired compound of formula (I). In other words, an amine having the formula (IV):

$$H_2N\text{-}L_a\text{-}Z_a$$

and/or an amine having the formula (V):

$$H_2N\text{-}L_b\text{-}Z_b$$

is reacted with the anhydride, thereby forming a naphthalene diimide intermediate.

As noted above, the compound of the invention can be symmetrical or asymmetrical. If it is desired to obtain a symmetrical compound of formula (I), that is, where the two pendant groups attached to the diimide scaffold are to be the same, then the dianhydride is reacted with one amine. In this case, the two nucleophilic sites on the dianhydride will be substituted by the same amine, thereby producing a symmetrical diimide intermediate. However, if an asymmetrical compound is to be obtained, two different types of amines may be used to react with the dianhydride.

In this reaction, the primary amine attacks the dianhydride. Without wishing to be bound by theory, the reaction may be classified as a nucleophilic substitution reaction. For the purpose of evaluating the reaction kinetics of the reaction, a commonly known mechanism, namely the substitution nucleophilic bimolecular ($SN_2$) mechanism, may be applicable. Regardless of the mechanistic route assumed, the reaction can be carried out as shown in the examples below.

In general, the molar proportions of the reagents employed in the reaction can be varied over a relatively wide range, the particular amount of each reactant to use being within the knowledge of those skilled in the art. For example, it is possible to react an excess of amines with a stoichiometrically smaller quantity of dianhydride. Conversely, it is also possible to react an excess of dianhydrides with a small quantity of amines.

The reaction can be carried out in any suitable vessel which provides sufficient contacting between the reactants. For simplicity, a stirred batch reactor can be employed. The reactants may be added to the reactor in any order. For example, it is possible to dissolve the primary amine(s) as mentioned above in a polar organic solvent, such as an ether, preferably cyclic ethers (e.g. oxiranes, oxetanes, and other cyclic ethers with 5 or more carbon atoms such as tetrahydrofuran). The sterically unhindered oxygen atom in ethers carries two unshared pairs of electrons, thus favouring the formation of coordination complexes and the solvation of cations. Subsequently, the dianhydride is added to the mixture, and the reaction mixture is stirred and refluxed at an elevated temperature for a suitable period of time to form the diimide intermediate.

Where a symmetrical compound of formula (I) is to be obtained, a single amine is reacted with the dianhydride. The diimide intermediate that is formed can be obtained directly through precipitation. For example, in one known method of preparation, an aqueous acetone is first introduced into the reaction mixture to dissolve the diimide intermediate after the reflux has been carried out for the desired period of time. Subsequently, anhydrous ether can be added to bring about the precipitation of the intermediate. If two amines are added to form an asymmetrical compound, the reaction product will contain both the symmetrical as well as the asymmetrical compound. In this case, it is possible to isolate the asymmetrical compound through any conventional means, such as solvent extraction or chromatography or a combination of such techniques. An efficient chromatographic separation technique can be achieved using an eluent that comprises a combination of polar solvents such as alcohols and halogenated hydrocarbons, e.g. trichloromethane, chloroform, dichloroethylene and tetrachloroethylene. Optionally, in order to further purify the isolated asymmetrical product, a suitable solvent can be added to the chromatographically separated asymmetrical compounds. The same eluent used in the chromatographic separation can be used as a solvent here. Nevertheless, the solvent can also be a different compound than the eluent. In any case, the asymmetrical compounds can then be extracted from the solvent mixture via solvent extraction, using an aqueous inorganic acid, such as hydrogen chloride, as the extraction solvent. The asymmetrical compound can be precipitated by adding an alkaline solution, e.g. aqueous ammonia, to the extract.

In specific embodiments of the invention, the first step of the reaction leads to the formation of the naphthalene diimide intermediates with the formula (VI):

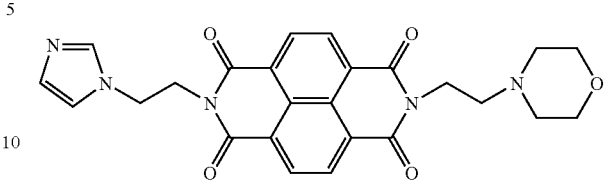

and the formula (VII)

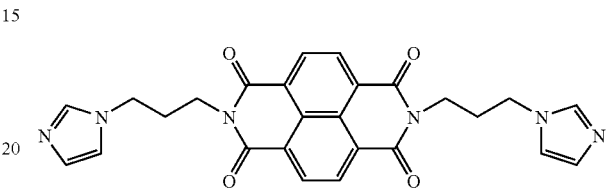

In the second reaction step, the naphthalene diimide derivative is reacted with a transition metal complex so that the transition metal complex becomes coordinatively bonded to any available coordination valence present in $Z_a$ and $Z_b$ via ligand exchange. In order to form asymmetrical compounds, it is possible to use a complexing moiety as either $Z_a$ or $Z_b$ which would not lead to any reaction with the transition metal complex. For example, if the coordination moiety does not have any available or suitable coordination valence, the metal complex will not be attached to the complexing moiety. In order for the transition metal complex to be bonded to the complexing moiety, the metal complex preferably comprises one or more weakly bonded ligands which can be easily displaced by the complexing moiety.

Another aspect of the invention concerns a method of detecting a nucleotide sequence in which compounds of the formula (I) are used as DNA threading intercalators. Electrochemical DNA biosensors constructed with compounds of formula (I) as electrocatalytic intercalators had good sensitivity, and in some embodiments, the sensitivity of detection under electrochemical analysis was able to detect a target DNA at concentrations as low as 100 fM. The method of the invention can drastically improve the practicability of electrochemical detection because no labelling procedures are required. The combination of the selective intercalation to ds-DNA with electrocatalysis of PIND-Os provides a simple, direct and yet highly sensitive non-labeling method for DNA quantification.

In the present method, the electrocatalytic activity of the transition metal groups in the compound of formula (I) is utilised to transduce the hybridisation event into an electrochemical signal. It has been found that compounds of the formula (I) not only intercalate strongly to the hybridised probe, they also retain their electrocatalytic activity while being intercalated onto the ds-DNA. This electrocatalytic activity can be easily detected, and is harnessed to serve as a highly sensitive indicator of hybridisation in the present method. In particular, rather than carrying out the measurement of current signals which are produced at the capture probe electrodes as is typically done, the present method utilises the electroactive properties of the transition metal groups in the compound to alter the electrochemical properties of a test reagent, so that when an electrochemical analysis is performed on the test reagent, changes in its electrochemical response would provide an indication of hybridisation. The test reagent can be any oxidizable and/or reducible organic compounds which have well-characterised oxidation and reduction behaviour. Examples of such compounds are alcohols, aldehydes and acids. In one presently preferred embodiment, the test reagent is ascorbic acid.

In carrying out this method, a sample assay containing, for example, a nucleic acid sequence can first be placed in a suitable medium. Desired probes may then be added, optionally accompanied by the addition of 1 or more recombinational enzymes to assist in the hybridisation. Hybridisation can be initiated by any appropriate means, for example, by the addition of ATP (adenosine triphosphate) and/or magnesium ions. Thereafter, a compound of formula (I) can be added to the assay so that intercalation of any hybridised probe present can take place. Subsequently, the probes are thoroughly washed to remove the non-intercalated compounds of formula (I), particularly those which may have become adsorbed onto the electrode surface. After washing, the probes may then be placed into the test reagent. An oxidising or reducing potential is applied to the test reagent, and the electrochemical response of the test reagent towards the potential is analysed, e.g. the oxidation/reduction potential, peak current, etc.

In order to determine the electrochemical response of the test reagent, any typical electrochemical detection method can be used. In presently preferred embodiments, the electrochemical detection methods are voltammetry or amperometry. If hybridization has occurred, characteristics of the test reagent such as voltammetric peak current and redox potential will be different from its characterised typical values.

In general, the compounds of the present invention can be used as DNA threading intercalators for the detection of various proteins, peptides and nucleic acids. However, they are not limited to such use but can be applied to any other suitable application requiring the use of electrocatalytic/electroactive compounds.

The following examples are offered in order to more fully illustrate the invention, but are not to be construed as limiting the scope thereof.

EXAMPLES

A general synthesis route for producing compounds of the present invention is shown in FIG. 1. This synthesis route has been applied in the following examples to demonstrate how specific examples of these compounds are made.

Example 1

Synthesis of N,N'-bis[1(3-propyl)-imidazole]-1,4,5, 8-naphthalene diimide (PIND) grafted with Os(bpy)$_2$ Cl$_2$ (PIND-Os)

A) Chemicals

1(3-aminopropyl)-imidazole (98%, Al) and 1,4,5,8-naphthalene tetracarboxylic dianhydride (>95%) were purchased from Sigma-Aldrich (St Louis, Mo., USA). 2,2'-bipyridine (99%) was obtained from Avocado Research Chemicals Ltd (Leysham Lancester, UK). All other reagents were obtained from Sigma-Aldrich and used without further purification. [Osmium(2,2'-bipyridine)$_2$Cl$_2$]Cl (Os(bpy)$_2$Cl$_2$), was synthesized from K$_2$OsCl$_6$ (99%, Stem Chemicals) following the proposed procedure by Lay. CPs used in this work were custom-made by Alpha-DNA (Montreal, Canada). All other oligonucleotides were custom-made by 1$^{st}$ Base Pte Ltd (Singapore). A phosphate-buffer saline (PBS, pH 7.4), consisted of 0.15 M NaCl and 0.020 M phosphate buffer, was used as the supporting electrolyte.

B) Equipment

Electrochemical experiments were carried out using a CH Instruments model 660A electrochemical workstation coupled with a low current module (CH Instruments, Austin, Tex.). The three-electrode system consisted of a 2-mm diameter gold working electrode, a miniature Ag/AgCl reference electrode (Cypress Systems, Lawrence, Kans.) and a platinum wire counter electrode. To avoid the spreading of the sample droplet beyond the 2-mm diameter working area, a patterned hydrophobic film was applied to the gold electrode after the immobilization of the CP. All potentials reported in this work were referred to the Ag/AgCl reference electrode. UV-visible spectra were recorded on an Agilent 8453 UV-visible spectrophotometer. Mass spectrometric experiments were performed with a Finnigan/MAT LCQ Mass Spectrometer (ThermoFinnigan, San Jose, Calif.). All spectra were recorded at room temperature unless otherwise noted.

C) Synthesis Procedure

The synthesis of PIND-Os is outlined in FIG. 1. PIND was prepared following a general procedure for the synthesis of ND. To a magnetically stirred mixture of 3.0 ml of Al and 3.0 ml of tetrahydrofuran was slowly added 0.30 g of 1,4,5,8-naphthalene tetracarboxylic dianhydride. The rate of addition was controlled so that there was little clogging. The reaction mixture was refluxed for 24 h and then cooled to room temperature. Next, it was dispersed in a 10 ml of acetone/water (3/1) mixture and then poured into a 500 ml of rapidly stirred anhydrous ether to precipitate the compound. The precipitate was collected by suction filtration through a fine fritted funnel and washed briefly with ethanol. Purification was performed by crystallization from chloroform and dried under vacuum at 40° C. overnight to give 0.28 g of dark red crystals.

PIND-Os was synthesized in a single-step ligand-exchange reaction. To a solution of Os(bpy)$_2$Cl$_2$ (0.32 g, 0.52 mmol) in 8.0 ml fresh-distilled ethylene glycol was added PIND (0.12 g, 0.25 mmol) in small portions over 10 min and the result mixture was refluxed for 20-40 min. The completion of the ligand-exchange reaction was monitored by cyclic voltammetry. The purple reaction mixture was then poured slowly into a 100 ml of rapid stirred ethanol saturated with KCl. The precipitate was collected by suction filtration through a fine fritted funnel. The crude product was washed with PBS, dissolved in 3.0-5.0 ml of ethanol and precipitated again from KCl saturated ethanol. The precipitate was further purified by crystallization from ethanol giving the pure product in 78% yield. The product showed a single pair of reversible redox waves at a glassy carbon electrode with an E$_{1/2}$ of 0.12 V in PBS. To ensure a complete double ligand-exchange at the two imidazole termini of PIND, slight excess of Os(bpy)$_2$ (5-10%) was provided.

Figure 3:
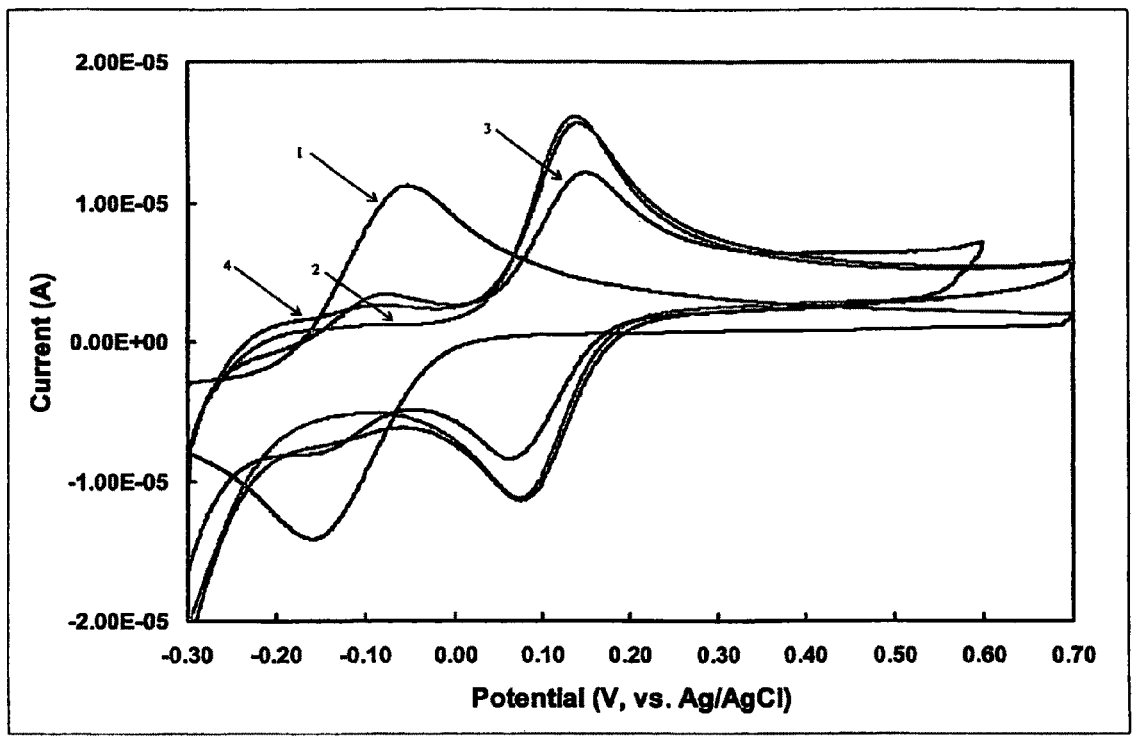
FIG. 3 shows a normalized cyclic voltammograms of Os(bpy)$_2$ (1) and PIND-Os (2); and Os(bpy)$_2$Cl$_2$ after 10 (3) and 30 min (4) of refluxing with PIND in ethylene glycol. PBS was used as the supporting electrolyte, and a potential scan rate of 100 mV/s was applied.

The formation of the electroactive PIND-Os intercalator can be conveniently monitored by cyclic voltammetry. During reflux in the ethylene glycol, cyclic voltammetric tests were conducted every 10 min. FIG. 3 shows typical voltammograms obtained in the first 30 min. As can be seen in FIG. 3 (trace 1), before adding PIND to Os(bpy)$_2$Cl$_2$, one pair of reversible voltammetric peaks centered at −0.11 V were obtained, corresponding to the well-known redox process of Os(bpy)$_2$Cl$_2$. Upon adding PIND, a new pair of voltammetric peaks appeared at 0.12 V, indicating the formation of PIND-Os (FIG. 3, trace 3). The two pairs of voltammetric peaks correspond to the two one-electron transfer processes of Os(bpy)$_2$Cl$_2$ and PIND-Os in the reaction mixture. Both electron transfer processes are clearly resolved and highly reversible. The intensity of the voltammetric peak at 0.12 V increased gradually with reaction time. Simultaneously, those at −0.11 V diminished gradually. Both of the redox pairs reached a steady-state after 30-40 min of refluxing (FIG. 3, trace 4) The minute voltammetric peaks at −0.11 V are indicative of the excess amount of Os(bpy)$_2$Cl$_2$. After separation and purification, voltammetric tests of the thus purified PIND-Os showed only one pair of voltammetric peaks implying that the purification process is very effective (FIG. 3, trace 2).

D) Characterisation of PIND-Os

Figure 4:
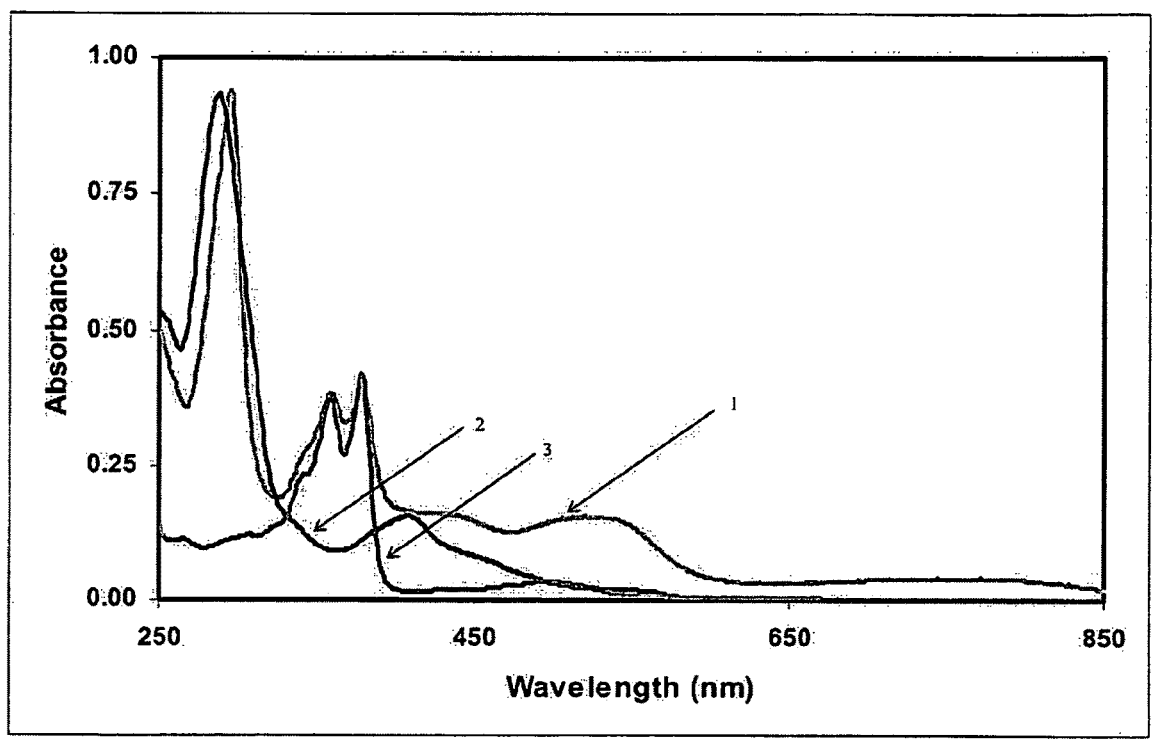
FIG. 4 shows a normalized UV-visible absorbance spectra of PIND-Os (1), Os(bpy)$_2$Cl$_2$(2) and PIND (3) in ethanol.

UV-visible absorbance spectra of the starting materials and PIND-Os are depicted in FIG. 4. The spectrum of PIND-Os is a composite of the absorbance spectra from both the ND moiety and the Os(bpy)$_2$Cl(Al) metal complex, as illustrated in the overlay of the spectra of the starting materials in ethanol. The visible region (400-600 nm) consists of the characteristic Os(d$\pi$)→bpy($\pi$*) metal-to-ligand charge transfer (MLCT) transition; the peaks at 383 and 362 nm are mainly due to $\pi \rightarrow \pi$* transition in PIND with some contribution from underlying MLCT absorbance. At shorter wavelength, the peak corresponds to ligand-centred transitions from both PIND and PIND-Os. The MLCT band for PIND-Os was broadened and shifted to the red in comparison to Os(bpy)$_2$Cl$_2$. This is likely a direct consequence of the ligand exchange which results in two types of MLCT transitions within the osmium complex: Os*→bpy, and Os*→Al. The imidazole groups of PIND are conjugated, resulting in a lower $\pi$* level for this ligand relative to the chloride of the complex.

It can be concluded from the UV results that the coupling between PIND and Os(bpy)$_2$Cl$_2$ results in a coordinative linkage and both imidazole termini of the PIND are grafted with Os(bpy)$_2$Cl$_2$.

Figure 6:
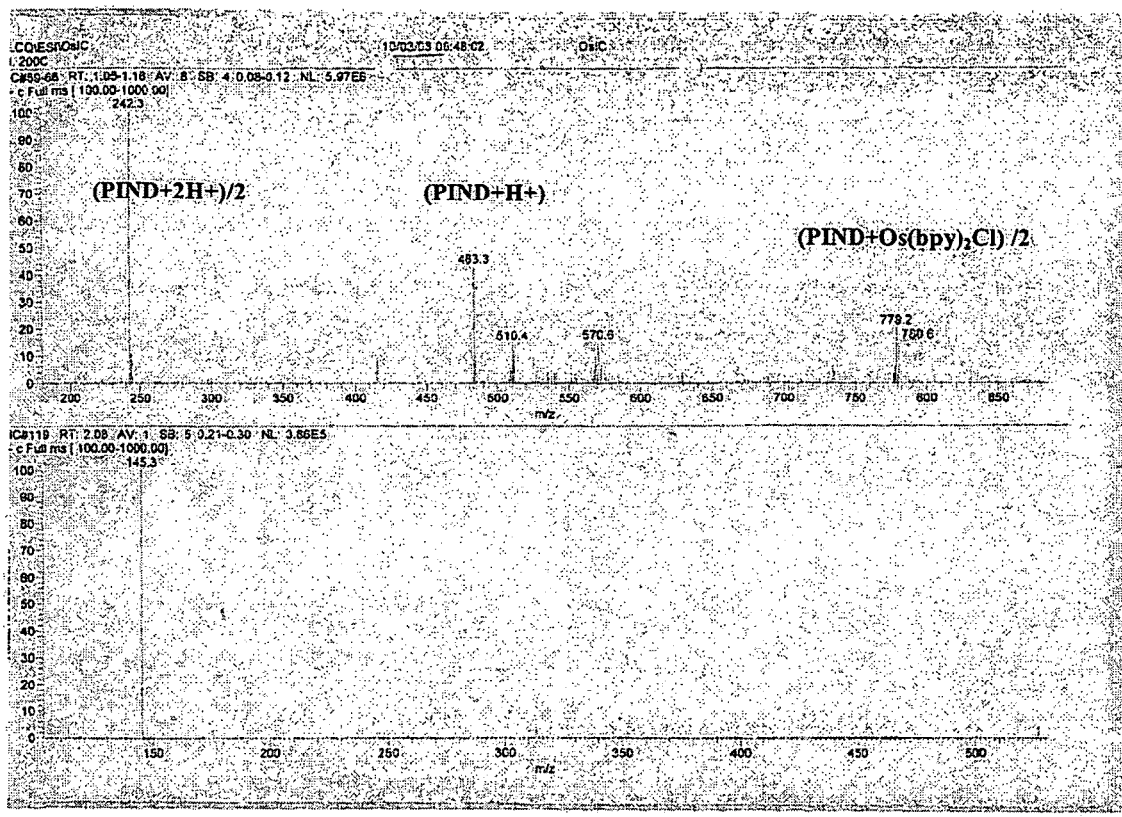
FIG. 6 shows an electron-spray ionization mass spectrum of PIND and PIND-Os.

A more direct proof of the formation of PIND-Os was derived a series of mass spectrometric tests on PIND and PIND-Os using electron-spray ionization mass spectrometry (ESI-MS). Predominant peaks were found at m/z 780, 483.3 and 242.3, corresponding to PIND-Os/2, PIND+H$^+$ and (PIND+2H$^+$)/2, respectively (FIG. 6). Since mono-grafted PIND was not observed in the ESI-MS spectrum, we can rule out any incomplete grafting of Os(bpy)$_2$Cl$_2$.

Electrochemical characterisation showed that PIND-Os exhibited exactly as expected for a highly reversible redox couple in solution. Little change was observed after numerous repetitive potential cycling between −0.30 V and +0.70V, revealing good stability of PIND-Os in solution. At slow scan rates, <500 mV/s, a typical diffusion-controlled voltammogram was recorded as expected for a one-electron exchange system exhibiting an ideal Nernstian behavior: the peak current is proportional to the square root of the potential scan rate, the peak-to-peak potential separation is very close to the theoretical value of 59 mV and potential scan rate independent. Such results ascertain that all of the osmium redox centres are allowed to reach the electrode surface and proceed to reversible heterogeneous electron transfer.

Example 2

DNA Detection Using PIND-Os: UV Spectrophotometry and Fluorescence Competition Experiment A) Immobilization of Capture Probes (CP)

Prior to CP immobilization, a gold electrode was thoroughly polished with 0.050 µm alumina slurry and sonicated in water for 10 min. It was then cleaned in an oxygen plasma for 5-10 min and immersed in absolute ethanol for 20 min to reduce the oxide layer. A CP monolayer was formed by immersing the gold electrode in a 100 µg/ml CP solution for 16-24 h. After adsorption, the electrode was copiously rinsed with PBS and soaked in PBS for 20 min, rinsed again, and blown dry with a stream of air, a procedure aimed at removing any non-specifically adsorbed materials. The density of CP, assessed electrochemically using cationic redox probes according to the procedure proposed by Steel, was found to be in the range of 1.13–1.30×10$^{-11}$ mol/cm$^2$. To minimize non-DNA related PIND-Os uptake and improve the quality and stability of the monolayer. The CP coated gold electrode was immersed in an ethanolic solution of 2.0 mg/ml 1-mercaptododecane (MD) for 4-6 h. Unreacted MD molecules were rinsed off and the electrode was washed by immersion in a stirred ethanol for 10 min and followed by thorough rinsing with ethanol and water. The electrode was ready after air-dry.

B) Hybridization

Figure 2:
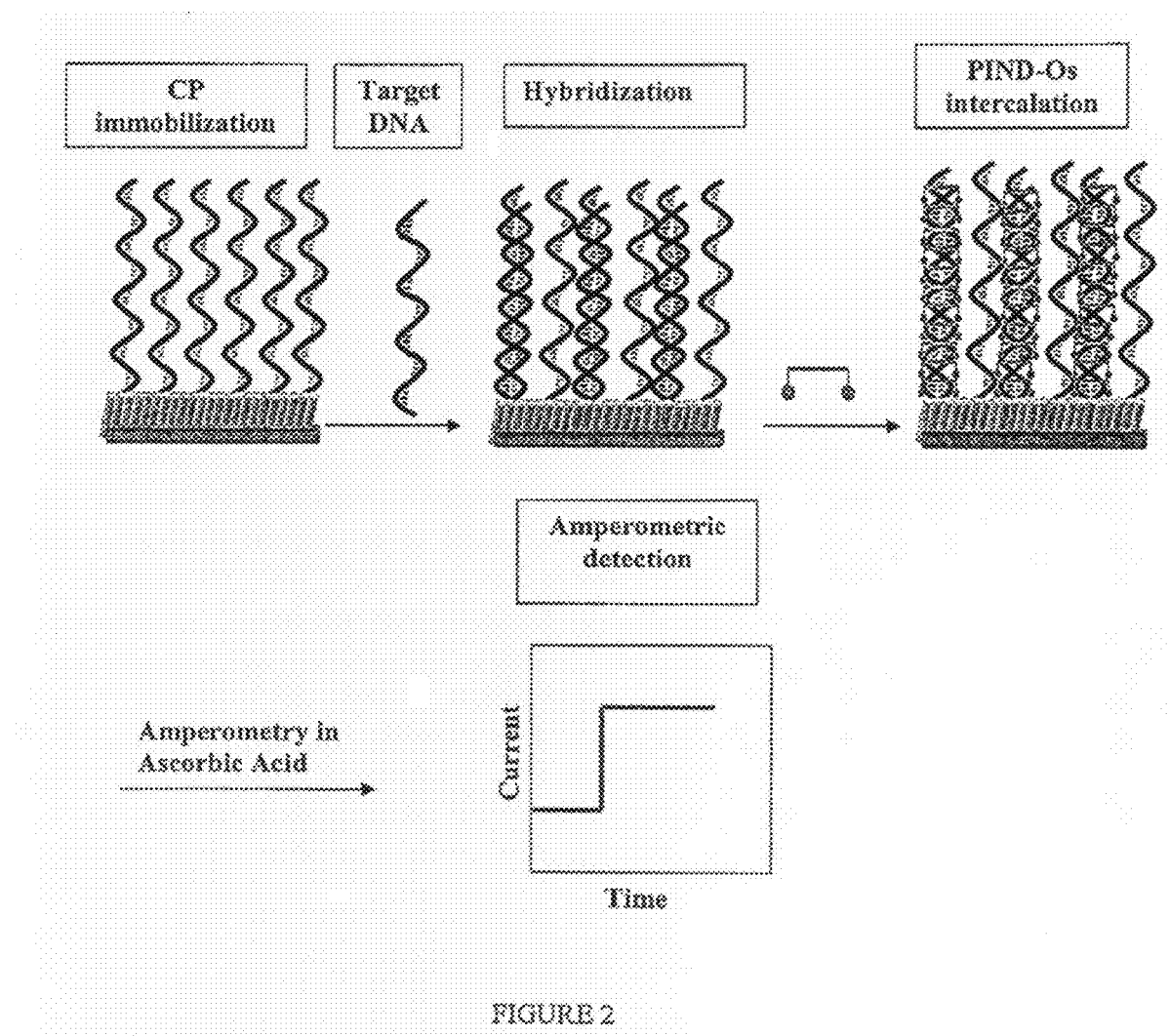
FIG. 2 is a schematic illustration of how a DNA assay in which compounds of the invention is used as intercalators for the detection of a target oligonucleotide sequence. The illustration shows a DNA biosensor's typical amperometric response in ascorbic acid.

The hybridization of a target DNA and its electrochemical detection were carried out in three steps, as depicted in the scheme in FIG. 2. First, the electrode was placed in a moisture saturated environmental chamber maintained at 53° C. A 2.5 µl aliquot of hybridization solution containing the target DNA was uniformly spread onto the electrode. It was then rinsed thoroughly with a blank hybridization solution at 53° C. and incubated at 35° C. for 10 min with a 5.0 µl aliquot of 100 µg/ml of PIND-Os in the hybridization solution. PIND-Os was attached to the hybridized target DNA via threading intercalation. It was then air-cooled and held at room temperature for 10 min before being thoroughly rinsed with a PBS saturated with NaCl. The AA electro-oxidation current was measured amperometrically in PBS containing 1.0 mM AA. At low DNA concentrations, smoothing was applied after each amperometric measurement to remove random noise and electromagnetic interference.

C) Detection

To determine the mode of interaction of PIND-Os with ds-DNA, UV-vis spectrophotometry of PIND-Os in the presence of increasing amounts of salmon sperm DNA were investigated. In the UV-Vis spectrophotometry, signatures of intercalative binding, where the fused plannar aromatic ring system of a threading intercalator inserts itself between the base pairs of the ds-DNA, are hypochromism are red shifts. As shown in FIG. 4, addition of DNA to PIND-Os at a DNA base pair/PIND-Os ratio of 4.0 resulted in a 35% decrease and a 3 nm-red shift of the ND band at 361 nm and 380 nm. The ND absorbance band hypochromism reached a plateau at the DNA base pair/PIND-Os ratio of less than 4.0 and constant hypochromism was observed for a ratio above 4.0, indicating that the binding of PIND-Os to ds-DNA takes place by preferential intercalation of the ND.

In order to obtain a better estimation of the intercalating property of the compounds of formula (I), a competition experiment was designed. The basis of this methodology involves the use of two intercalators, one fluorescent and one non-fluorescent. The fluorescent intercalator first saturates the ds-DNA. Then a second intercalator, in this case PIND-Os, is introduced into the system with gradual increasing concentration. For the competition experiment, the changes in fluorescent intensity was monitored during the displacement of ds-DNA-bound fluorescent molecules by PIND-Os through an increasing concentration of PIND-Os molecules in the system. A well known threading intercalator, ethidium bromide (EB), was chosen as the control fluorescent indicator. EB has been widely studied as an efficient DNA intercalator and is one of the most popular fluorescent intercalators used in DNA assays. EB displays a 25-fold fluorescence enhancement upon binding to the ds-DNA, which provides sufficient sensitivity and good discrimination against free EB molecules in fluorescent measurement. In addition, the kinetics of EB intercalation is quite fast, which significantly shortens the time needed to reach equilibrium.

To ensure that our approach is appropriate for this study, an increasing concentration (0-100 µM) of a well-studied non-fluorescent intercalator, naphthalene diimide (ND) was first added to the EB saturated ds-DNA solution, gel electrophoretic experiments showed that the fluorescent intensity of the EB intercalated with ds-DNA diminished gradually as the concentration of ND increased. The binding constant, $K_d$ of $4.0 \times 10^5$, estimated from the experimental data, was in good agreement with literature value. Subsequently, PIND-Os was studied with respect to its ability to compete against EB for binding to ds-DNA using the same approach. Different amounts of PIND-Os were mixed with the EB saturated ds-DNA to examine the bind ability.

Figure 8A:
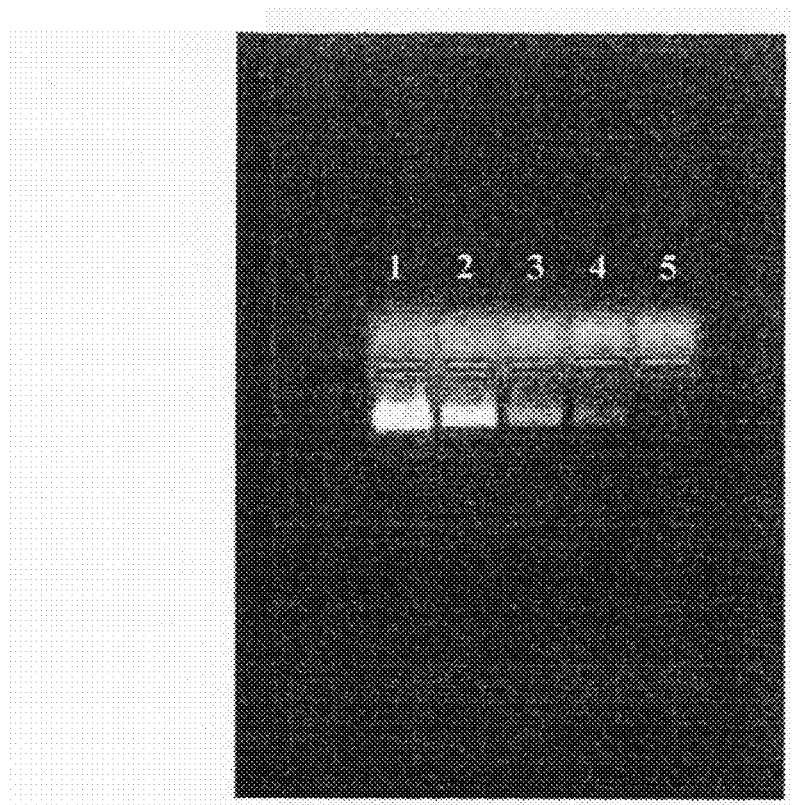
FIG. 8A shows the gel electrophoretic results showing the dsDNA binding property of PIND-Os. The following ratios of PIND-Os to EB were used from lanes 1 to 5: 0/40, 2/40, 5/40, 10/40 and 20/40.

As shown in FIG. 8A, PIND-Os exhibited a remarkable binding affinity towards ds-DNA. Lanes 1 to 5 correspond to different ratios of PIND-Os/EB. The higher the ratio of PIND-Os/EB, the lower the fluorescent intensity. The lower fluorescent intensities of the ds-DNA obtained with the higher ratios of PIND-Os/EB (lanes 2-5) suggested that more PIND-Os molecules are bound to the ds-DNA and larger amounts of EB molecules are replaced. As shown by the second lane, at a PIND-Os/EB molecular ratio of as low as 1/8, more than 50% of the ds-DNA-bound EB was replaced, as evidenced by the diminished fluorescent intensity of intercalated EB and the increased fluorescent intensity of free EB, suggesting that PIND-Os is a much stronger DNA intercalator than EB. The binding constant $K_d$, estimated from the experimental data, was $6.1 \times 10^6$, corresponding to approximately a 15-fold enhancement over ND. A plausible explanation for the stability constant enhancement would be that after the ND group has intercalated with ds-DNA, the two cationic Os(bpy)$_2$Cl groups in PIND-Os form ion-pairs with phosphate each side of the ds-DNA, making ND more tightly fixed in between the base pairs of ds-DNA. In addition, a closer examination of the gel image showed that accompanying the weakening of fluorescent intensity, there was a systematic change in DNA mobility. The higher the ratio of PIND-Os/EB, the higher the band appeared in the gel image, and in turn, the slower the mobility of the DNA. The molecular mass of EB is 324 and that of PIND-Os is 1560, as determined by mass spectrometry. In addition, PIND-Os is dicationic. Obviously, the lower mobility is caused by the bulky and dicationic nature of PIND-Os.

Example 3

DNA Detection Using PIND-Os: Voltammetric Analysis of the Hybridised Complex

PIND-Os was evaluated as the electroactive indicator for possible applications in DNA sensing. A hybridization test was carried out using a poly(A) oligonucleotide as the target DNA. Upon hybridization with a poly(T) CP coated electrode, the target DNA was selectively bound to its complementary CP and became fixed on the sensor surface. Thorough rinsing with the hybridization buffer washed off all of the non-hybridization related DNA. PIND-Os was brought to the sensor surface during a subsequent incubation with a PIND-Os solution.

Figure 8B:
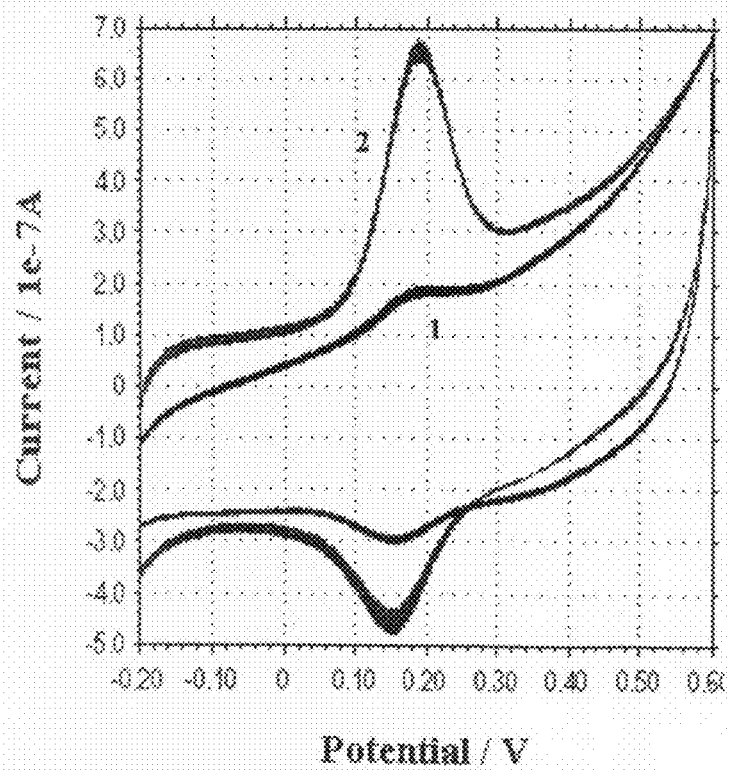
FIG. 8B shows the cyclic voltammograms of PIND-Os bound to a poly(T) oligonucleotide coated electrode before (1) and after (2) hybridization with 50 nM of poly(A) oligonucleotide. PBS was used as the supporting electrolyte, and a potential scan rate of 100 mV/s was applied.

Cyclic voltammograms for the CP modified electrodes before and after hybridization with its complementary DNA are shown in FIG. 8B. Before hybridization, one pair of minute voltammetric peaks were observed at the redox potential of PIND-Os (FIG. 8B, (1)). After hybridization, a slight positive shift in the redox potential was observed and the peak current increased by as much as 20-fold. It was found that extensive washing with NaCl saturated PBS removed most of the non-DNA related PIND-Os uptake. These results clearly demonstrated that PIND-Os selectively interacts with ds-DNA and the PIND-Os-ds-DNA adduct has a very slow dissociation rate, which paves the way for developing a highly sensitive DNA biosensors. Therefore, using the intercalated PIND-Os as an electroactive indicator for direct detecting DNA was evaluated. A detection limit of 1.5 nM was obtained.

Example 4

Figure 9:
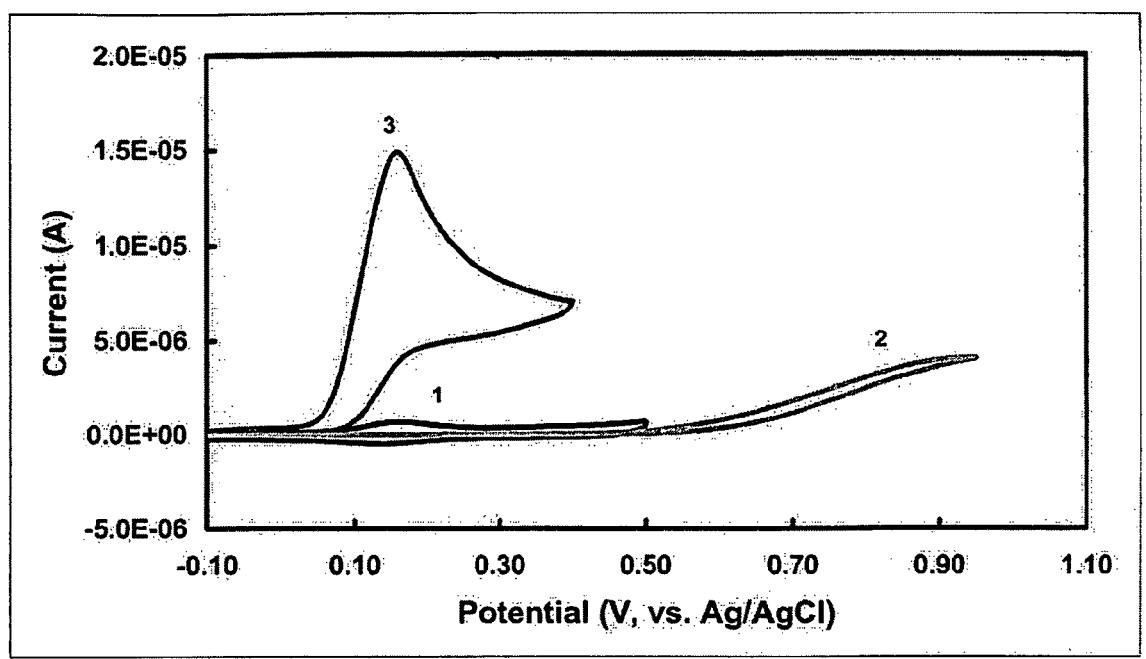
FIG. 9 shows the cyclic voltammograms of ascorbic acid bound to a poly(T) oligonucleotide coated electrode before (2) and after (3) hybridization with 5.0 nM of poly(A) oligonucleotide and intercalation with PIND-Os. PBS in a 1.0 mM ascorbic acid solution was used as the supporting electrolyte, and a potential scan rate of 100 mV/s was applied. Trace (1) was obtained from a target DNA hybridised sensor in blank PBS for comparison.

DNA Detection Using PIND-Os: Voltammetric and Amperometric Analysis of an Organic Acid in the Presence of the Intercalated Complex In another test, the completed sensors before and after hybridization with the target DNA were tested voltammetrically and amperometrically in PBS containing AA. FIG. 9 shows cyclic voltammograms of AA before and after hybridization. For comparison, a target DNA hybridized sensor in blank PBS is also presented (FIG. 9 trace 1). Trace 2 was obtained with the sensor before hybridization and without PIND-Os incubation, while trace 3 corresponds to the sensor after hybridization and PIND-Os intercalation. Both sensors showed a totally irreversible oxidation process for AA. Before hybridization the anodic peak potential ($E_p$) for AA oxidation was about 0.90V, largely due to the presence of MD and anionic CP. Both of them impede electron exchange between the underlying electrode and AA. It can be seen that the presence of PIND-Os greatly reduced the overpotential of AA oxidation, shifting the $E_p$ value negatively by as much as 0.74 V to 0.16 V. The oxidation current prior to the peak rose rapidly and the peak current was enhanced about 4-fold. The oxidation potential is similar to that reported for such a process at osmium-bipyridine redox polymer modified electrode. Part of the reason for the drastic improvement is due to the reduced electrostatic repulsion since some of the negative charges are neutralized by the intercalated PIND-Os. More importantly, the much improved voltammetric response after PIND-Os intercalation is due to a genuine catalytic effect of the Os(bpy)$_2$Cl moieties. The increase in peak current and the decrease in the anodic overpotential demonstrated an efficient electrocatalysis of AA. The shift in the overpotential is due to a kinetic effect, hence greatly increased the rate of electron transfer from AA to the electrode, which is attributed to the improvement in the reversibility of the electron transfer processes. It was found that the catalytic current is proportional to the target DNA concentration in the range of 0.030-10 nM with a detection limit of 0.020 nM, 75-fold higher that of the direct voltammetric detection of intercalated PIND-Os. Higher catalytic current was observable with increasing AA concentration, but with very little improvement in detection limit, owing to a simultaneous increase in background current.

Figure 10:
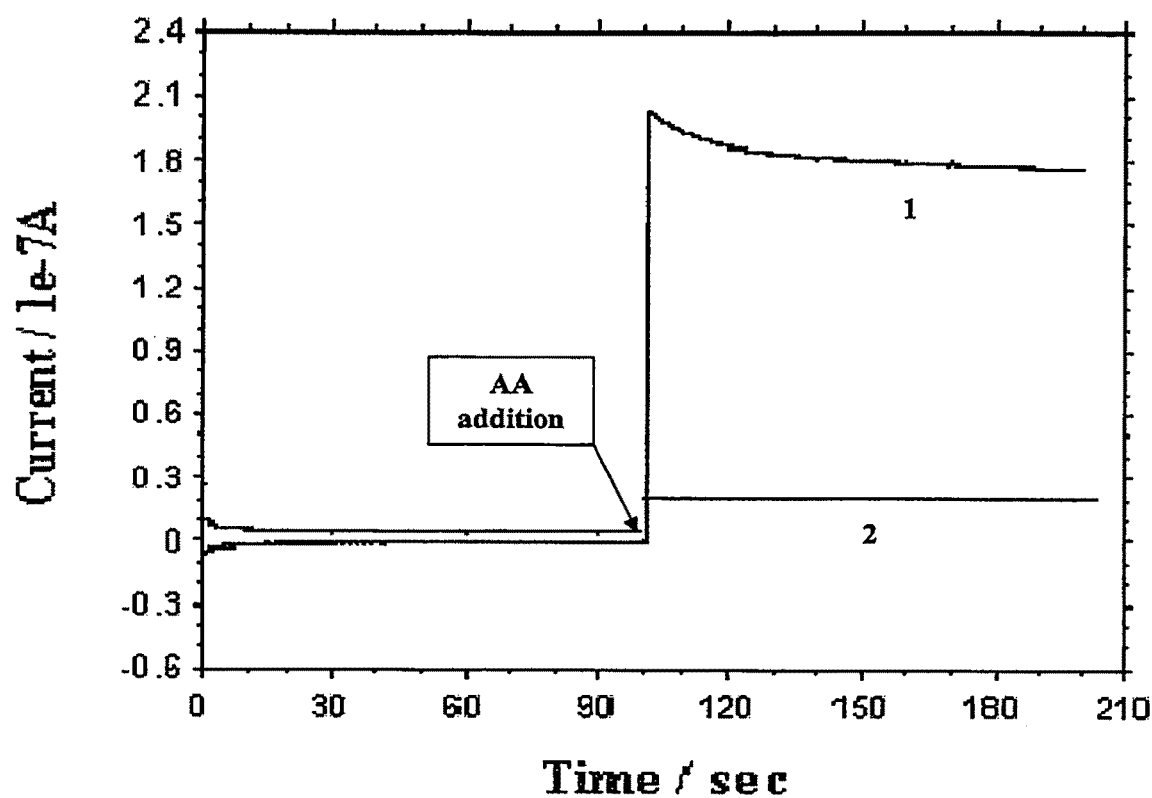
FIG. 10 shows the amperometric responses of PIND-Os bound to a poly(T) oligonucleotide coated electrode before (1) and after (2) hybridization with 50 pM of poly(A) oligonucleotide. PBS was used as the supporting electrolyte, and a poise potential of 0.20 V was applied.

On the basis of the above voltammetric investigations, it appears highly likely that better analytical characteristics can be achieved in amperometry. A feature of the electrocatalysis that appears to be particularly promising is the low potential at which AA oxidation takes place. Amperometric detection at significantly lower operating potentials minimizes potential interferants and reduces background current yielding improved signal-to-noise ratio and lower detection limit. As shown in FIG. 10, the oxidation current in amperometry increased by 0.18 μA at 0.20 V upon the addition of 1.0 mM AA to PBS (FIG. 10 trace 1). In a control experiment where non-complementary CP, poly(A), were immobilized on the sensor surface, only a 0.017 μA increment was observed (FIG. 10, trace 2). The amperometric data agreed well with the voltammetric results obtained earlier and confirmed again that the target DNA was successfully detected with high specificity and sensitivity. A linear relationship between the amperometric oxidation current and the target DNA concentration was observed in the range of 0.20-600 pM with a correlation coefficient of 0.992, The detection limit, defined as a signal-to-noise ratio of 3, was found to be 100 fM, more than 1000-fold improvement in sensitivity over direct voltammetry.

Example 5

Synthesis of unsymmetrical intercalators-N-[1-(3-propyl)-imidazole]-N'[-1(3-propyl)-morpholine)]1,4,5,8-naphthalene diimide (PPND)

A) Chemicals and Equipment

N-(3-aminopropyl)-morpholine was obtained from Sigma-Aldrich (St. Louis, Mo., USA). All other chemicals and equipment used in this example were identical to those used in Example 1.

B) Synthesis Procedure

An asymmetrical compound of formula (I), PPND, was prepared according to the procedure outlined as follows. Briefly, to a magnetically stirred mixture of 1.0 ml of N-(3-aminopropyl)-morpholine, 0.60 ml N-(3-aminopropyl)-imidazole and 10 ml of tetrahydrofuran was slowly added 0.40 g of 1,4,5,8-naphthalene tetracarboxylic dianhydride. The rate of addition was controlled so that there was little clogging. The reaction mixture was refluxed for 24 hours and then cooled to room temperature. The reaction mixture was evaporated and purified by silica gel chromatography with use of a 1:1 ($CHCl_3$: ethanol) mis-solvent eluent. The second band of the chromatographic separation comprises mainly of the asymmetrical compound. It was collected, evaporated, and further purified using solvent extraction. Solvent extraction was carried out by dissolving the chromatographically obtained product in trichloromethane $CHCl_3$ and then extracted with 0.020M HCl. The pure asymmetrical compound was precipitated out with the addition of 10% aqueous $NH_3$. It was then dried under vacuum at 40° C. overnight to give 0.18 g of dark red crystals.

C) Characterisation of PPND-Os

Figure 5:
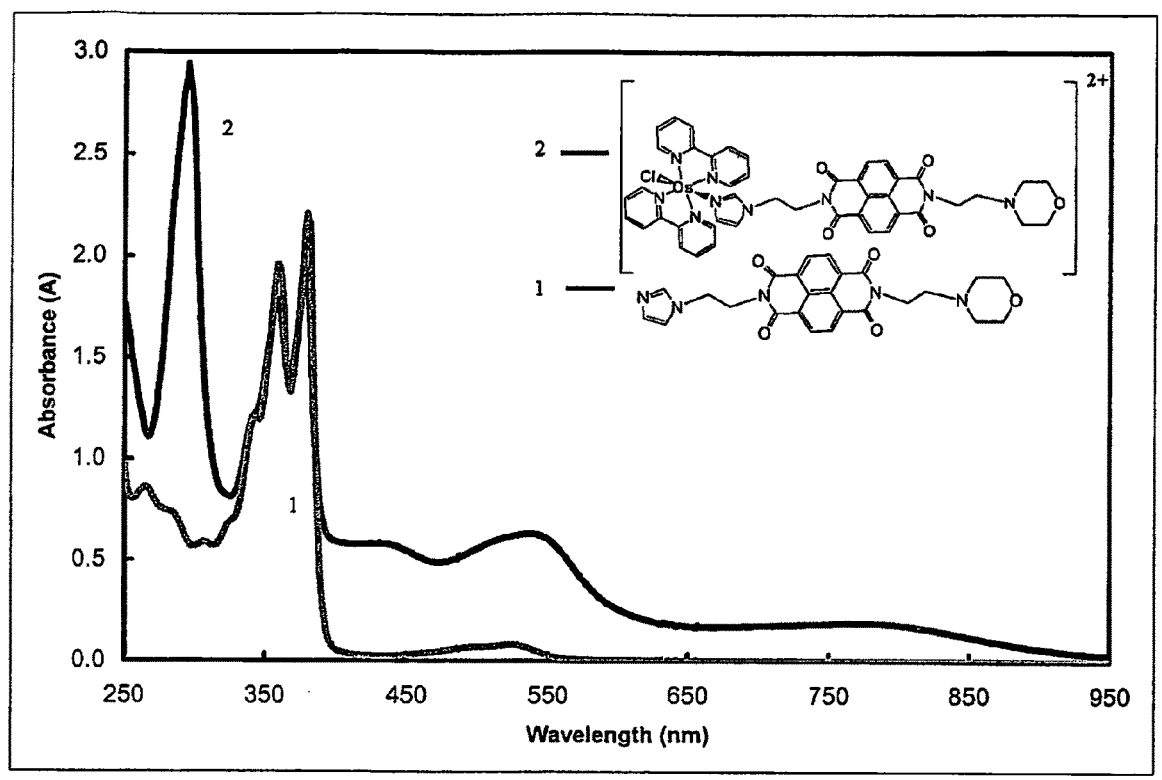
FIG. 5 shows a normalised UV-visible spectra of PPND (1) and PPND-Os (2) in ethanol.
Figure 7:
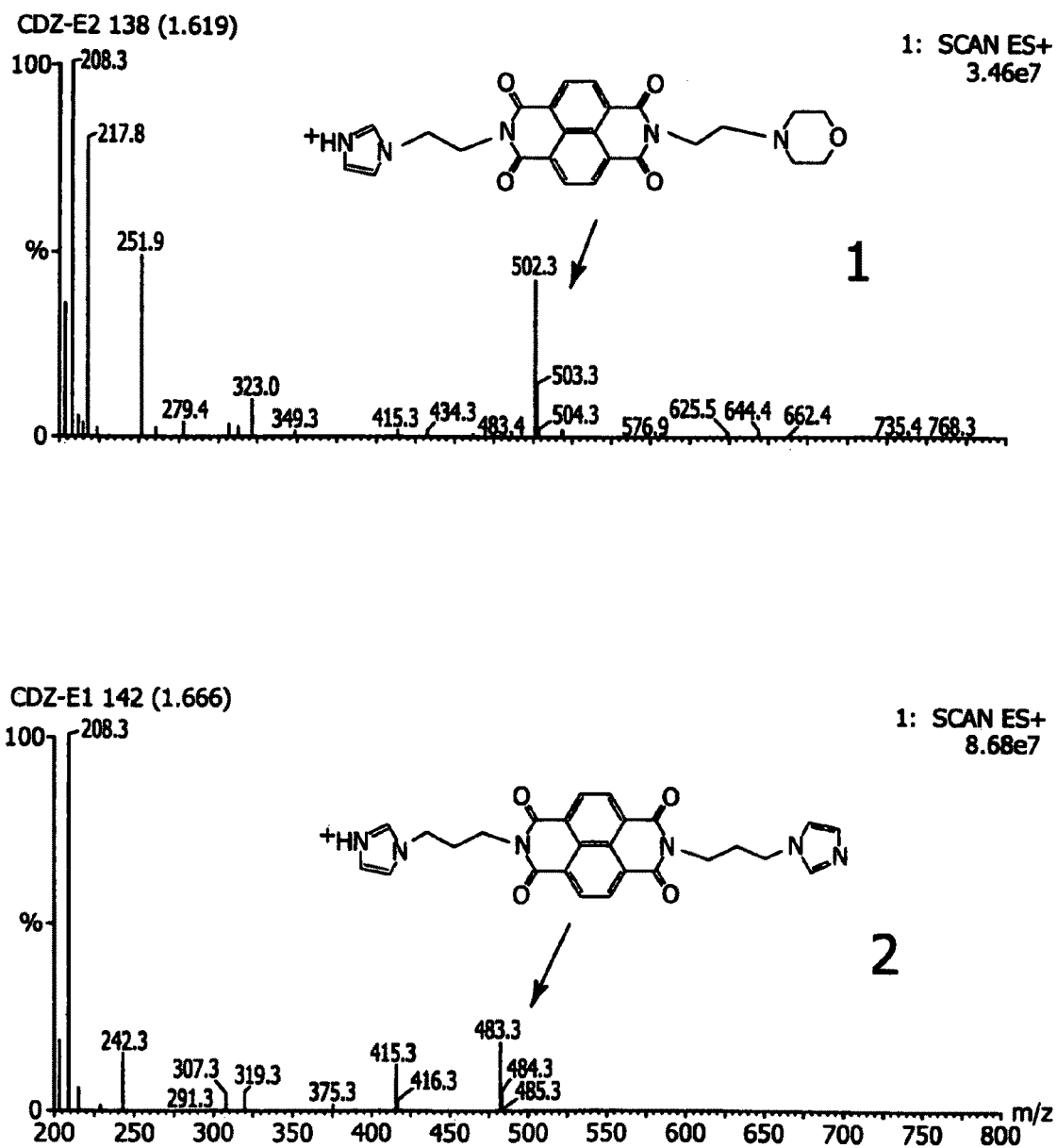
FIG. 7 shows an electron-spray ionization mass spectrum of PPND (1) and PIND (2).

HPLC-mass spectra reveals that the isolated crystals were pure (yield: 24%) (FIG. 7). UV-visible absorbance spectra of PPND and PPND-Os are depicted in FIG. 5. The spectrum of PPND-Os is a composite of the absorbance spectra from both the ND moiety and the $Os(bpy)_2Cl$ metal complex. The visible region (400-600 nm) consists of the characteristic $Os(d\pi) \rightarrow bpy(\pi^*)$ metal-to-ligand charge transfer (MLCT) transition; the peaks at 383 and 362 nm are mainly due to $\pi \rightarrow \pi^*$ transition in PPND with some contribution from underlying MLCT absorbance. At shorter wavelength, the peak corresponds to ligand-cantered transitions from both PPND and PPND-Os.

What is claimed is:

1. A compound having the general formula (I):

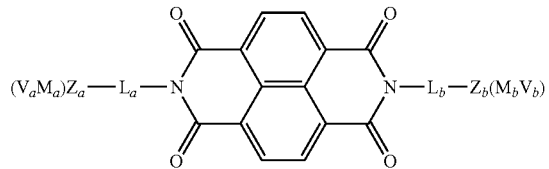

wherein
each of $L_a$ and $L_b$ is independently selected from a linking moiety comprising 0 to 10 main chain atoms, optionally substituted;
each of $Z_a$ and $Z_b$ is an independently selected complexing moiety comprising at least one nitrogen atom,
wherein each of the complexing moieties $Z_a$ and $Z_b$ is a heterocycle selected from the group consisting of, pyrazine, acridine, azepine, aziridine, benzodiazine, bipyridine, diazine, isoquinoline, lactam, oxazine, phenanthridine, phenanthroline, piperazine, pteridine, purine, pyridine, pyrrole, pyrrolidine, quinoline, quinolizine, thiadiazine, thiazine, triazine and tropane;
either both or one of $Z_a$ and/or $Z_b$ is coordinatively bonded to a respective transition metal complex $M_aV_a$ and/or $M_bV_b$ by said nitrogen atom, wherein
each of $M_a$ and $M_b$ is an independently selected transition metal, wherein each of the transition metals $M_a$ and $M_b$ is independently selected from the group consisting of osmium, iron, rhenium, and platinum, and
each of $V_a$ and $V_b$ is an independently selected valence group.

2. The compound of claim 1, wherein each of $L_a$ and $L_b$ is an aliphatic saturated hydrocarbon chain.

3. The compound of claim 1, wherein each of the valence groups $V_a$ and $V_b$ is independently selected from the group consisting of halide, pyridine, bipyridine, phenanthroline, imidazole, dipyridophenazine, porphyrin and derivatives thereof.

4. The compound of claim 1, wherein $Z_a$ and $Z_b$ are identical.

5. The compound of claim 4, wherein $Z_a$ and $Z_b$ are selected from the group consisting of purine, piperazine, phenanthroline and pyridine.

6. The compound of claim 1, wherein $Z_a$ and $Z_b$ are different.

7. The compound of claim 1, wherein $L_a$ and $L_b$ are identical.

8. The compound of claim 7, wherein $L_a$ and $L_b$ are ethyl or propyl.

9. The compound of claim 1, wherein only one transition metal complex $M_aV_a$ is present.

10. The compound of claim 1, wherein two transition metal complexes $M_aV_a$ and $M_bV_b$ are present.

11. The compound of claim 10, wherein said $M_b$ is identical to $M_a$.

12. The compound of claim 9, wherein the transition metal $M_a$ is osmium, and the valence group $V_a$ consists of two bypyridine (bpy) ligands and one halogen ligand.

13. A process for producing a compound having the general formula (I):

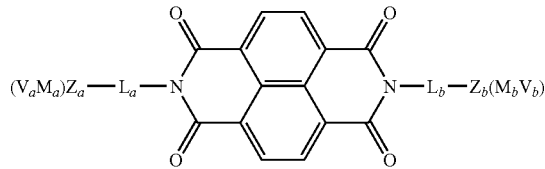

wherein
  each of $L_a$ and $L_b$ is independently selected from a linking moiety comprising 0 to 10 main chain atoms, optionally substituted;
  each of $Z_a$ and $Z_b$ is an independently selected complexing moiety comprising at least one nitrogen atom; wherein each of the complexing moiety $Z_a$ and $Z_b$ is a heterocycle selected from the group consisting of triazine, pyrazine, acridine, azepine, aziridine, benzodiazine, bipyridine, diazine, isoquinoline, lactam, oxazine, phenanthridine, phenanthroline, piperazine, pteridine, purine, pyridine, pyrrole, pyrrolidine, quinoline, quinolizine, thiadiazine, thiazine, and tropane;
  either both or one of $Z_a$ and/or $Z_b$ is coordinatively bonded to a respective transition metal complex $M_aV_a$ and/or $M_bV_b$ through said nitrogen atom, wherein
  each of $M_a$ and $M_b$ is an independently selected transition metal,
  wherein each of the transition metals $M_a$ and $M_b$ is independently selected from the group consisting of osmium, iron, rhenium, and platinum, and
  each of $V_a$ and $V_b$ is an independently selected valence group,
  said process comprising:
  reacting 1,4,5,8-naphthalene tetracarboxylic dianhydride with a primary amine having the formula (IV):

and/or a primary amine having the formula (V):

thereby forming a naphthalene diimide intermediate; and
  reacting the naphthalene diimide intermediate with a transition metal complex, thereby coordinatively bonding the metal complex to the at least one nitrogen atom in each of $Z_a$ and/or $Z_b$.

14. The method of intercalating a compound having the formula (I) as defined in claim 1 into double stranded DNA comprising contacting the DNA with a compound having the formula (I) as defined in claim 1.

15. A method of detecting a nucleic acid, comprising:
  contacting at least one capture probe immobilised on a substrate with the nucleic acid, said capture probe having a nucleotide sequence complementary to the sample, thereby hybridising the nucleic acid to the capture probe to form a hybrid;
  contacting the hybrid with a DNA threading intercalator compound having the general formula (I):

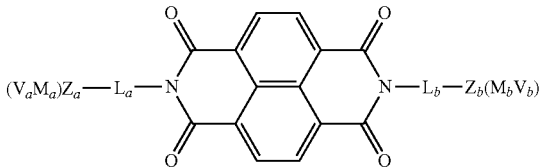

wherein
  each of $L_a$ and $L_b$ is an independently selected from a linking moiety comprising 0 to 10 main chain atoms, optionally substituted;
  each of $Z_a$ and $Z_b$ is an independently selected complexing moiety comprising at least one nitrogen atom; wherein each of the complexing moiety $Z_a$ and $Z_b$ is a heterocycle selected from the group consisting of, pyrazine, acridine, azepine, aziridine, benzodiazine, bipyridine, diazine, isoquinoline, lactam, oxazine, phenanthridine, phenanthroline, piperazine, pteridine, purine, pyridine, pyrrole, pyrrolidine, quinoline, quinolizine, thiadiazine, thiazine, triazine and tropane;
  said one or both of $Z_a$ and/or $Z_b$ is coordinatively bonded to a respective transition metal complex $M_aV_a$ and/or $M_bV_b$ through said nitrogen atom, wherein
  each of $M_a$ and $M_b$ is an independently selected transition metal, wherein each of the transition metals Ma and Mb is independently selected from the group consisting of osmium, iron, rhenium, and platinum, and
  each of $V_a$ and $V_b$ is an independently selected valence group,
  thereby intercalating the hybrid;
  contacting an organic acid with the intercalated hybrid;
  applying an oxidising or reducing potential to the organic acid; and
  determining the electrochemical response of the organic acid.

16. The method of claim 15, wherein the organic acid is ascorbic acid.

17. The method of claim 15, wherein the electrochemical response of the organic acid was determined by voltammetry or amperometry.

* * * * *